US010299686B2

(12) United States Patent
Arnon et al.

(10) Patent No.: US 10,299,686 B2
(45) Date of Patent: May 28, 2019

(54) METHOD APPARATUS AND SYSTEM FOR ANALYZING IMAGES

(75) Inventors: Israel Boaz Arnon, Neve Tsuf (IL); Yoel Arieli, Jerusalem (IL)

(73) Assignee: Real Imaging Ltd., Airport City (IL)

(*) Notice: Subject to any disclaimer, the term of this patent is extended or adjusted under 35 U.S.C. 154(b) by 0 days.

(21) Appl. No.: 12/934,647

(22) PCT Filed: Dec. 28, 2008

(86) PCT No.: PCT/IL2008/001684
§ 371 (c)(1),
(2), (4) Date: Sep. 26, 2010

(87) PCT Pub. No.: WO2009/118721
PCT Pub. Date: Oct. 1, 2009

(65) Prior Publication Data

US 2011/0021944 A1 Jan. 27, 2011

Related U.S. Application Data

(60) Provisional application No. 61/064,823, filed on Mar. 28, 2008.

(51) Int. Cl.
*A61B 1/00* (2006.01)
*A61B 5/00* (2006.01)
*A61B 5/01* (2006.01)

(52) U.S. Cl.
CPC .................................... *A61B 5/015* (2013.01)

(58) Field of Classification Search
CPC ........................................................ A61B 5/00
USPC ......... 600/474, 473, 315, 549; 382/154, 128
See application file for complete search history.

(56) References Cited

U.S. PATENT DOCUMENTS

| | | | | |
|---|---|---|---|---|
| 5,314,249 | A | 5/1994 | Marui et al. | |
| 5,946,425 | A | 8/1999 | Bove, Jr. et al. | |
| 5,961,466 | A | 10/1999 | Anbar | |
| 6,094,198 | A | 7/2000 | Shashua | |
| 6,167,151 | A | 12/2000 | Albeck et al. | |
| 6,201,541 | B1 | 3/2001 | Shalom et al. | |
| 6,442,419 | B1 * | 8/2002 | Chu et al. | 600/474 |
| 6,603,988 | B2 * | 8/2003 | Dowlatshahi | A61B 5/06 600/407 |
| 6,701,081 | B1 | 3/2004 | Dwyer et al. | |

(Continued)

FOREIGN PATENT DOCUMENTS

| | | |
|---|---|---|
| DE | 10150918 | 5/2003 |
| EP | 2238572 | 10/2010 |

(Continued)

OTHER PUBLICATIONS

International Preliminary Report on Patentability dated Jul. 15, 2010 From the International Bureau of WIPO Re. Application No. PCT/IL2008/001683.

(Continued)

*Primary Examiner* — May A Abouelela

(57) ABSTRACT

A method of identifying a thermally distinguishable region in a living body is disclosed. The method comprises determining transient thermal history of a surface of the living body, and estimating a location or presence of the thermally distinguishable region in the living body based on the transient thermal history.

21 Claims, 20 Drawing Sheets
(1 of 20 Drawing Sheet(s) Filed in Color)

(56) References Cited

U.S. PATENT DOCUMENTS

| | | | | |
|---|---|---|---|---|
| 6,765,607 | B2 | 7/2004 | Mizusawa et al. | |
| 6,801,257 | B2 | 10/2004 | Segev et al. | |
| 6,850,862 | B1 | 2/2005 | Chidichinto et al. | |
| 6,965,690 | B2 | 11/2005 | Matsumoto | |
| 6,978,168 | B2 * | 12/2005 | Beatty | A61B 5/04085 600/513 |
| 7,027,621 | B1 * | 4/2006 | Prokoski | G06K 9/00255 180/272 |
| 7,072,504 | B2 * | 7/2006 | Miyano et al. | 382/154 |
| 7,292,719 | B2 * | 11/2007 | Arnon | 382/128 |
| 7,778,693 | B2 * | 8/2010 | Barbour et al. | 600/473 |
| 7,996,066 | B2 | 8/2011 | Schlagheck et al. | |
| 8,021,300 | B2 | 9/2011 | Ma et al. | |
| 8,620,041 | B2 | 12/2013 | Arnon et al. | |
| 2001/0046316 | A1 | 11/2001 | Miyano et al. | |
| 2004/0039268 | A1 * | 2/2004 | Barbour et al. | 600/310 |
| 2004/0151365 | A1 | 8/2004 | An Chang et al. | |
| 2004/0176804 | A1 | 9/2004 | Palti | |
| 2004/0236225 | A1 * | 11/2004 | Murphy et al. | 600/473 |
| 2005/0096515 | A1 | 5/2005 | Geng | |
| 2005/0113651 | A1 | 5/2005 | Wood et al. | |
| 2006/0285731 | A1 | 12/2006 | Jiang et al. | |
| 2007/0051889 | A1 | 3/2007 | Yannacone et al. | |
| 2007/0110293 | A1 | 5/2007 | Arnon | |
| 2007/0161922 | A1 | 7/2007 | Dekel et al. | |
| 2007/0166284 | A1 | 7/2007 | Rasmussen et al. | |
| 2007/0213617 | A1 * | 9/2007 | Berman | A61B 5/0091 600/473 |
| 2007/0293792 | A1 * | 12/2007 | Sliwa et al. | 600/587 |
| 2009/0024023 | A1 * | 1/2009 | Welches et al. | 600/424 |
| 2009/0030302 | A1 * | 1/2009 | Taniguchi et al. | 600/410 |
| 2010/0172567 | A1 * | 7/2010 | Prokoski | A61B 5/0064 382/132 |
| 2010/0191541 | A1 * | 7/2010 | Prokoski | A61B 5/0064 705/2 |
| 2014/0112561 | A1 | 4/2014 | Arnon et al. | |

FOREIGN PATENT DOCUMENTS

| | | | |
|---|---|---|---|
| GB | 2358752 | 8/2001 | |
| JP | 2001-318003 | 11/2001 | |
| JP | WO2006135003 | * 12/2006 | A61B 6/524 |
| JP | 2007-525244 | 9/2007 | |
| WO | WO 2004/098392 | 11/2004 | |
| WO | WO 2006/003658 | 1/2006 | |
| WO | WO 2009/083973 | 7/2009 | |
| WO | WO 2009/083974 | 7/2009 | |
| WO | WO 2009/118721 | 10/2009 | |

OTHER PUBLICATIONS

International Preliminary Report on Patentability dated Jul. 15, 2010 From the International Bureau of WIPO Re. Application No. PCT/IL2008/001685.

International Search Report dated Jun. 2, 2009 From the International Searching Authority Re.: Application No. PCT/IL2008/001683.

International Search Report dated Apr. 14, 2009 From the International Searching Authority Re.: Application No. PCT/IL2008/001684.

International Search Report dated May 18, 2009 From International Searching Authority Re.: Application No. PCT/IL2008/001685.

Written Opinion dated Jun. 2, 2009 From the International Searching Authority Re.: Application No. PCT/IL2008/001683.

Written Opinion dated Apr. 14, 2009 From the International Searching Authority Re.: Application No. PCT/IL2008/001684.

Written Opinion dated May 18, 2009 From the International Searching Authority Re.: Application No. PCT/IL2008/001685.

Agostini et al. "Evaluation of Feature-Based Registration in Dynamic Infrared Imaging for Breast Cancer Diagnosis", Proceedings of the 28th IEEE EMBS (Engineering in Medicine and Biology) Annual International Conference, New York City, USA, Aug. 30-Sep. 3, 2006, XP031235634, p. 953-956, Aug. 30, 2006. p. 953, § 2, 3.

Aksenov et al. "3D Thermography for Quantification of Heat Generation Resulting From Inflammation", Proceedings of the 8th 3D Modelling Symposium, Paris, France, XP))2523191, 11 P., 2003.

Bichinho et al. "A Computer Tool for the Fusion and Visualization of Thermal and Magnetic Resonance Images", Journal of Digital Imaging [Online], XP002527797, Retrieved From the Internet: URL:http://www.springerlink.com/content/5w157t2747272m65/>. p. 3, col. 1, Line 5-col. 2, Line 6, Fig.1.

Deng et al. "Enhancement of Thermal Diagnostics on Tumors Underneath the Skin by Induced Evaporation", Proceedings of the 2005 27th Annual International Conference of the Engineering in Medicine and Biology Society, Shanghai, China, Sep. 1-4, 2005, IEEE-EMBS 2005, XP002519610, 7: 7525-7528, 2005. Passage Bridging p. 7526 and p. 7527, Abstract, Figs.4, 5.

Deng et al. "Mathematical Modeling of Temperature Mapping Over Skin Surface and Its Implementation in Thermal Disease Diagnostics", Computers in Biology and Medicine, XP002523192, 34(6): 495-521, Sep. 2004. Abstract, p. 497.

Kaczmarek et al. "Optical Excitation Methods in Active Dynamic Thermography in Medical Diagnostics", Proceedings of the SPIE—The International Society for Optical Engineering SPIE, XP002519609, 5566(1): 120-126, 2004. p. 121, Last §, p. 123, First §, Fig.3.

Lipari et al. "Advanced Infrared Image Processing for Breast Cancer Risk Assessment", Proceedings of the 19th Annual International Conference of the IEEE/EMBS Engineering in Medicine and Biology Society, Chicago, IL, USA, Oct. 30-Nov. 2, 1997, XP010325780, 2: 673-676, Oct. 30, 1997. Abstract, Sections II, III, Fig.3.

Moderhak et al. "Problems of 3D Breast Imaging", Gdansk University of Technology, Department of Biomedical Engineering, 2 P.

Tan et al. "A Novel Cognitive Interpretation of Breast Cancer Thermography With Complementary Learning Fuzzy Neural Memory Structure", Expert Systems With Applications, XP005919120, 33(3): 652-666, Mar. 13, 2007. Abstract, p. 658-659, Section 4, Fig.5.

Response dated Jun. 21, 2011 to Communication Pursuant to Article 94(3) EPC dated Dec. 21, 2010 From the European Patent Office Re. Application No. 08866783.7.

Communication Pursuant to Article 94(3) EPC dated Aug. 16, 2011 From the European Patent Office Re. Application No. 08873559.2.

Agostini et al. "Evaluation of Feature-Based Registration in Dynamic Infrared Imaging for Breast Cancer Diagnosis", Proceedings of the 28th IEEE EMBS (Engineering in Medicine and Biology) Animal International Conference, New York City, USA, Aug. 30-Sep. 3, 2006, XP031235634, p. 953-956, Aug. 30, 2006. p. 953, § 2, 3.

International Preliminary Report on Patentability dated Oct. 7, 2010 From the International Bureau of WIPO Re. Application No. PCT/IL2008/001684.

Communication Pursuant to Article 94(3) EPC dated Dec. 21, 2010 From the European Patent Office Re. Application No. 08866783.7.

Communication Pursuant to Article 94(3) EPC dated Jan. 12, 2011 From the European Patent Office Re. Application No. 08867385.0.

Response dated Jul. 12, 2011 to Communication Pursuant to Article 94(3) EPC dated Jan. 12, 2011 From the European Patent Office Re. Application No. 08867385.0.

Translation of Office Action dated Jun. 22, 2011 From the State Intellectual Property Office of the People's Republic of China Re. Application No. 200880127685.9.

Communication Pursuant to Article 94(3) EPC dated Apr. 25, 2013 From the European Patent Office Re. Application No. 08867385.0.

Translation of Office Action dated Dec. 14, 2012 From the State Intellectual Property Office of the People's Republic of China Re. Application No. 200880127684.4.

Wedemeyer et al. "Numerical Simulation of the Three-Dimensional Structure and Dynamics of the Non-Magnetic Solar Chromosphere", Astronomy & Astrophysics, 414(3): 1121-1137, Feb. 2004.

Official Action dated Jun. 19, 2013 From the US Patent and Trademark Office Re. U.S. Appl. No. 12/811,097.

Bichinho et al. "A Computer Tool for the Fusion and Visualization of Thermal and Magnetic Resonance Images", Journal of Digital Imaging, 22(5): 527-534, Oct. 2009.

(56) References Cited

OTHER PUBLICATIONS

Notice of Allowance dated Oct. 16, 2013 From the US Patent and Trademark Office Re. U.S. Appl. No. 12/811,097.
Office Action dated Sep. 8, 2013 From the Israel Patent Office Re. Application No. 206663 and Its Translation Into English.
Translation of Decision on Rejection dated Aug. 6, 2013 From the State Intellectual Property Office of the People's Republic of China Re. Application No. 200880127684.4.
Office Action dated Oct. 31, 2013 From the Israel Patent Office Re. Application No. 206644 and Its Translation Into English.
Supplemental Notice of Allowability dated Nov. 19, 2013 From the US Patent and Trademark Office Re. U.S. Appl. No. 12/811,099.
Communication Under Rule 71(3) EPC dated Jan. 31, 2014 From the European Patent Office Re. Application No. 08867385.0.
Official Action dated Jan. 25, 2013 From the US Patent and Trademark Office Re. U.S. Appl. No. 12/811,099.
Translation of Notice of Reason for Rejection dated Dec. 21, 2012 From the Japanese Patent Office Re. Application No. 2010-541136.
Translation of Notice of Reason for Rejection dated Dec. 21, 2012 From the Japanese Patent Office Re. Application No. 2010-541137.
Sato et al. "Image Guidance of Breast Cancer Surgery Using 3-D Ultrasound Images and Augmented Reality Visualization", IEEE Transactions on Medical Imaging, 17(5): 681-693, Oct. 1998.
Requisition by the Examiner dated Mar. 11, 2014 From the Canadian Intellectual Property Office Re. Application No. 2,710,941.
Office Action dated Oct. 20, 2013 From the Israel Patent Office Re. Application No. 208274 and Its Translation Into English.
Communication Pursuant to Article 94(3) EPC dated Feb. 8, 2012 From the European Patent Office Re. Application No. 08867385.0.
Communication Pursuant to Article 94(3) EPC dated Oct. 18, 2012 From the European Patent Office Re. Application No. 08873559.2.
Office Action dated Dec. 2, 2012 From the Israel Patent Office Re. Application No. 206644 and Its Translation Into English.
Official Action dated Nov. 19, 2012 From the US Patent and Trademark Office Re. U.S. Appl. No. 12/811,097.
Translation of Office Action dated Feb. 22, 2012 From the State intellectual Property Office of the People's Republic of China Re. Application No. 200880127684.4.
Barone et al. "A Biomedical Application Combining Visible and Thermal 3D Imaging", INGEGRAF (Asociacion Espanola de Ingenicria Grafica) 2006, Retrieved From the Internet, p. 1-9, 2006.
Wikipedia "Surface Integral", Wikipedia, the Free Encyclopedia, Retrieved From the Internet, 3 P., Jan. 23, 2012.
Notice of Reason for Rejection dated Feb. 28, 2014 From the Japanese Patent Office Re. Application No. 2010-541137 and Its Translation Into English.
Osman et al. "Thermal Modeling of the Normal Woman's Breast", Transactions of the ASME, Journal of Biomechanical Engineering, 106(2): 123-130, May 1984.
Requisition by the Examiner and the Examination Search Report dated Apr. 2, 2015 From the Canadian Intellectual Property Office Re. Application No. 2,710,941.
Official Action dated Dec. 12, 2014 From the US Patent and Trademark Office Re. U.S. Appl. No. 14/142,988.
Notice of Reason for Rejection dated Feb. 20, 2015 From the Japanese Patent Office Re. Application No. 2010-541136 and Its Translation Into English.
Requisition by the Examiner dated Jun. 8, 2015 From the Canadian Intellectual Property Office Re. Application No. 2,710,939.
Notice of Reason for Rejection dated Dec. 4, 2015 From the Japanese Patent Office Re. Application No. 2015-020950 and Its Translation Into English.
Official Action dated Dec. 31, 2015 From the US Patent and Trademark Office Re. U.S. Appl. No. 14/142,988.
Notice of Reexamination dated Oct. 9, 2016 From the Patent Reexamination Board of State Intellectual Property Office of the People's Republic of China Re. Application No. 200880127684.4 and Its Translation Into English.
Notice of Reexamination dated Feb. 14, 2016 From the Patent Reexamination Board of State Intellectual Property Office of the People's Republic of China Re. Application No. 200880127684.4 and Its Translation Into English.
Communication Pursuant to Article 94(3) EPC dated Sep. 9, 2016 From the European Patent Office Re. Application No. 08866783.7.
Office Action dated Mar. 2, 2017 From the State Intellectual Property Office of the People's Republic of China Re. Application No. 200880127684.4 and Its Translation of the Notification of Office Action Into English.) (43 Pages).
Communication Pursuant to Article 94(3) EPC dated Jun. 1, 2017 From the European Patent Office Re. Application No. 08866783.7. (6 Pages).
Examination Report Under Sections 12 & 13 of the Patents Act, 1970 and the Patents Rules, 2003 dated Dec. 22, 2017 From the Government of India, Intellectual Property India, Patents, Designs, Trade Marks, Geographical Indications Re. Application No. 1524/MUMNP/2010. (6 Pages).
Examination Report Under Sections 12 & 13 of the Patents Act, 1970 and the Patents Rules, 2003 dated Jun. 11, 2018 From the Government of India, Intellectual Property India, Patents, Designs, Trade Marks, Geographical Indications Re. Application No. 1523/MUMNP/2010. (7 Pages).
Communication Pursuant to Article 94(3) EPC dated Jul. 4, 2018 From the European Patent Office Re. Application No. 08866783.7. (7 Pages).
Burcher et al. "Deformation Correction in Ultrasound Images Using Contact Force Measurements", Mathematical Methods in Biomedical Image Analysis, XP010584860, 63-70, Dec. 9, 2001.
Carter et al. "A Framework for Image-Guided Breast Surgery", Medical Imaging and Augmented Reality Lecture Notes in Computer Science, XP019038094, 203-210, Jan. 1, 2006.
Washington et al. "Modality Independent Elastography (MIE): A New Approach to Elasticity Imaging", IEEE Transactions on Medical Imaging, XP011117917, 23(9): 1117-1128, Sep. 2004.

* cited by examiner

METHOD APPARATUS AND SYSTEM FOR ANALYZING IMAGES

RELATED APPLICATIONS

This Application is a National Phase of PCT Patent Application No. PCT/IL2008/001684 having International filing date of Dec. 28, 2008, which claims the benefit of U.S. Provisional Patent Application No. 61/064,823 filed on Mar. 28, 2008. The contents of the above Applications are all incorporated herein by reference.

FIELD AND BACKGROUND OF THE INVENTION

The present invention, in some embodiments thereof, relates to thermal images and, more particularly, but not exclusively, to the analysis of thermal images.

The use of imaging in diagnostic medicine dates back to the early 1900s. Presently there are numerous different imaging modalities at the disposal of a physician allowing imaging of hard and soft tissues and characterization of both normal and pathological tissues.

Infra red imaging is utilized for characterizing a thermally distinguishable site in a human body for the purposes of identifying inflammation. Infrared cameras produce two-dimensional images known as thermographic images. A thermographic image is typically obtained by receiving from the body of the subject radiation at any one of several infrared wavelength ranges and analyzing the radiation to provide a two-dimensional temperature map of the surface. The thermographic image can be in the form of either or both of a visual image and corresponding temperature data. The output from infrared cameras used for infrared thermography typically provides an image comprising a plurality of pixel data points, each pixel providing temperature information which is visually displayed, using a color code or grayscale code. The temperature information can be further processed by computer software to generate for example, mean temperature for the image, or a discrete area of the image, by averaging temperature data associated with all the pixels or a sub-collection thereof.

Based on the thermographic image, a physician diagnoses the site, and determines, for example, whether or not the site includes an inflammation while relying heavily on experience and intuition.

U.S. Pat. No. 7,072,504 discloses an approach which utilizes two infrared cameras (left and right) in combination with two visible light cameras (left and right). The infrared cameras are used to provide a three-dimensional thermographic image and the visible light cameras are used to provide a three-dimensional visible light image. The three-dimensional thermographic and three-dimensional visible light images are displayed to the user in an overlapping manner.

International Patent Publication No. 2006/003658, the contents of which are hereby incorporated by reference, discloses a system which includes non-thermographic image data acquisition functionality and thermographic image data acquisition functionality. The non-thermographic image data acquisition functionality acquires non-thermographic image data, and the thermographic image data acquisition functionality acquires thermographic image data.

U.S. Pat. No. 7,292,719, the contents of which are hereby incorporated by reference discloses a system for determining presence or absence of one or more thermally distinguishable objects in a living body. A combined image generator configured combines non-thermographic three-dimensional data of a three-dimensional tissue region in the living body with thermographic two-dimensional data of the tissue region so as to generate three-dimensional temperature data associated with the three-dimensional tissue region.

Also of interest is U.S. Pat. No. 6,442,419 disclosing a scanning system including an infrared detecting mechanism which performs a 360° data extraction from an object, and a signal decoding mechanism, which receives electrical signal from the infrared detecting mechanism and integrates the signal into data of a three-dimensional profile curved surface and a corresponding temperature distribution of the object.

Additional background art includes U.S. Pat. No. 6,850,862 which discloses the generation of three-dimensional maps of temperature distribution, and U.S. Pat. No. 5,961,466 which discloses detection of breast cancer from a rapid time series of infrared images which is analyzed to detect changes in the distribution of thermoregulatory frequencies over different areas of the skin.

SUMMARY OF THE INVENTION

According to an aspect of some embodiments of the present invention there is provided a method of identifying a thermally distinguishable region in a living body. The method comprises: determining transient thermal history of a surface of the living body, and estimating a location or presence of the thermally distinguishable region in the living body based on the transient thermal history.

According to some embodiments of the invention the determination of transient thermal history comprises obtaining a series of thermospatial representations describing a section of the living body, and extracting the transient thermal history of the body section based on thermal variations among the series.

According to some embodiments of the invention the method further comprising estimating a size of the internal thermally distinguishable region, based on the transient thermal history.

According to some embodiments of the invention the method further comprising comparing the transient thermal history to a reference transient thermal history, so as to determine the likelihood for the presence of the thermally distinguishable region.

According to an aspect of some embodiments of the present invention there is provided a method of treating a tumor in a body section, the tumor being an internal thermally distinguishable region in the body section. The method comprises (a) executing selected steps of the method described above so as to estimate a size of the tumor; (b) applying a destructive treatment to the tumor; and (c) executing selected steps of the method described above to re-estimate the size.

According to still further features in the described preferred embodiments the method further comprises repeating the (b) and the (c) until the size satisfies a predetermined criterion.

According to an aspect of some embodiments of the present invention there is provided a method of monitoring evolution of a tumor in a body section. The tumor being an internal thermally distinguishable region in the body section. The method comprises executing selected steps of the method described above a plurality of times to estimate a size of the tumor at each execution, thereby monitoring the evolution of the tumor.

According to an aspect of some embodiments of the present invention there is provided apparatus for locating a thermally distinguishable region within a living body. The apparatus comprises: an input unit for receiving a series of thermospatial representations describing a section of a living body; and a computing platform configured for extracting transient thermal history of the body section based on thermal variations present in the series and estimating a location or presence of an internal thermally distinguishable region in the body section based on the transient thermal history.

According to an aspect of some embodiments of the present invention there is provided an imaging and processing system, comprising the apparatus described above and a thermospatial imaging system operable to provide the input unit with the series of thermospatial representations.

According to some embodiments of the invention the apparatus further comprises a size estimator, configured for estimating a size of the internal thermally distinguishable region, based on the transient thermal history.

According to some embodiments of the invention the computing platform is configured for comparing the transient thermal history to a reference transient thermal history, so as to determine the likelihood for the presence of the thermally distinguishable region.

According to some embodiments of the invention at least two thermospatial representations of the series describe the body section while having at least two different shapes.

According to some embodiments of the invention a change in an ambient temperature at a surface of the body section is imposed between at least two successive thermospatial representations of the series.

According to some embodiments of the invention the location of the internal thermally distinguishable region is estimated by determining amount of temperature change for each point of a plurality of points over a surface of the body section.

According to some embodiments of the invention the location of the internal thermally distinguishable region is estimated by determining a temperature change rate for the point.

According to some embodiments of the invention the location of the internal thermally distinguishable region is estimated by comparing a temperature change rate of one point of the plurality of points to a temperature change rate of another point of the plurality of points.

According to some embodiments of the invention the location of the internal thermally distinguishable region is estimated by determining onset of a steady thermal state for the point.

According to some embodiments of the invention the location of the internal thermally distinguishable region is estimated by determining onset of temperature change for the point.

According to still further features in the described preferred embodiments the method further comprises calculating a deformation function mapping one shape of the at least two different shapes to another shape of the at least two different shapes. According to some embodiments of the invention the computing platform is configured for calculating a deformation function which maps one shape of the at least two different shapes to another shape of the at least two different shapes.

According to some embodiments of the invention the extraction of the transient thermal history is done by selecting a set of points belonging to one thermospatial representation of the series, utilizing the deformation function for determining a corresponding set of points belonging to another thermospatial representation of the series, and determining an individual thermal variation for each point in the set.

According to some embodiments of the invention the method further comprises estimating characteristic heat conduction of the body section based on the series. According to some embodiments of the invention the computing platform is configured for estimating characteristic heat conduction of the body section based on the series.

According to some embodiments of the invention the body section is a breast of a woman.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1B:
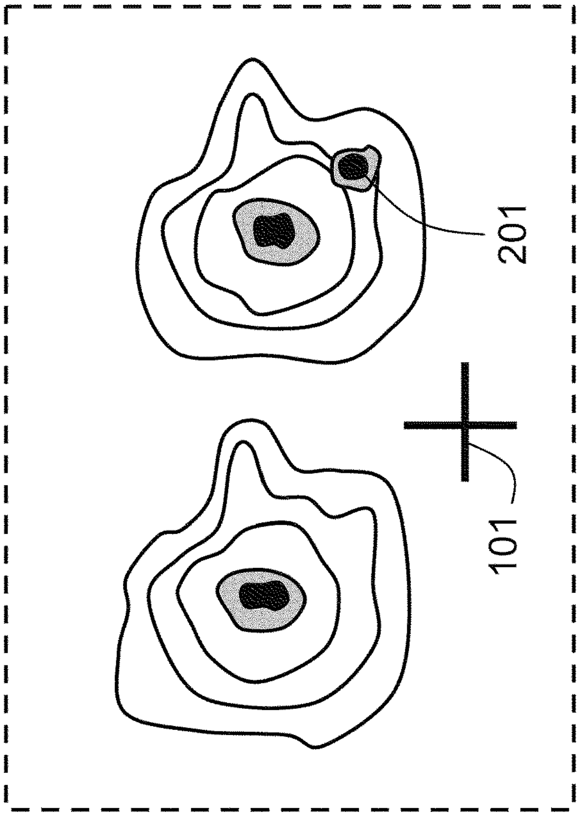
Figure 1A:
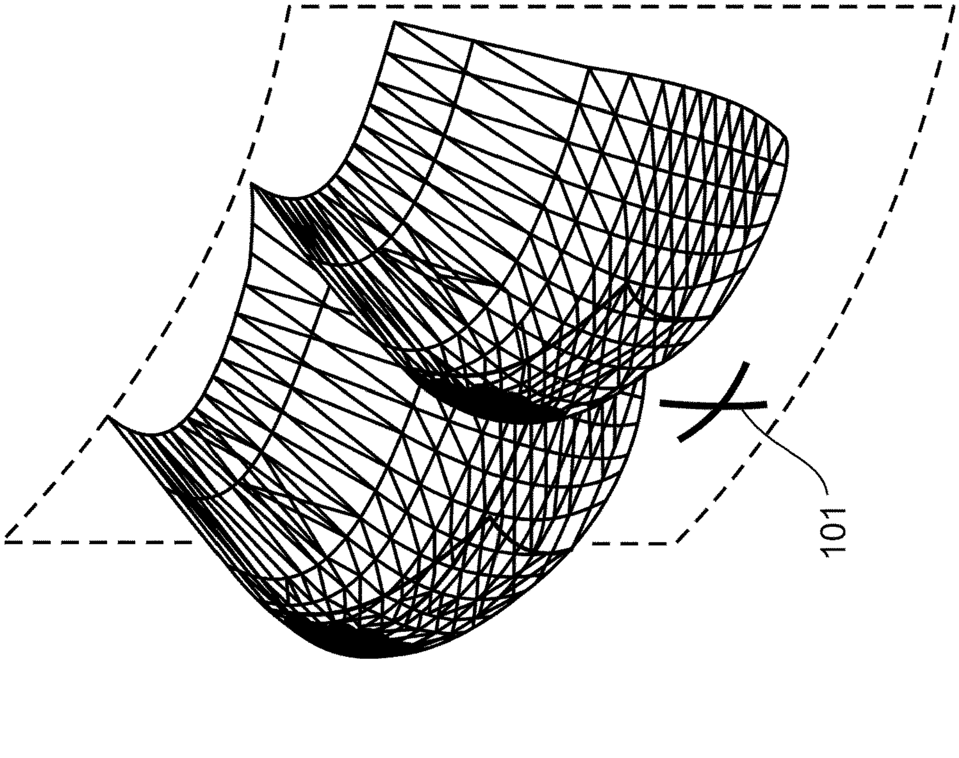
Figure 1C:
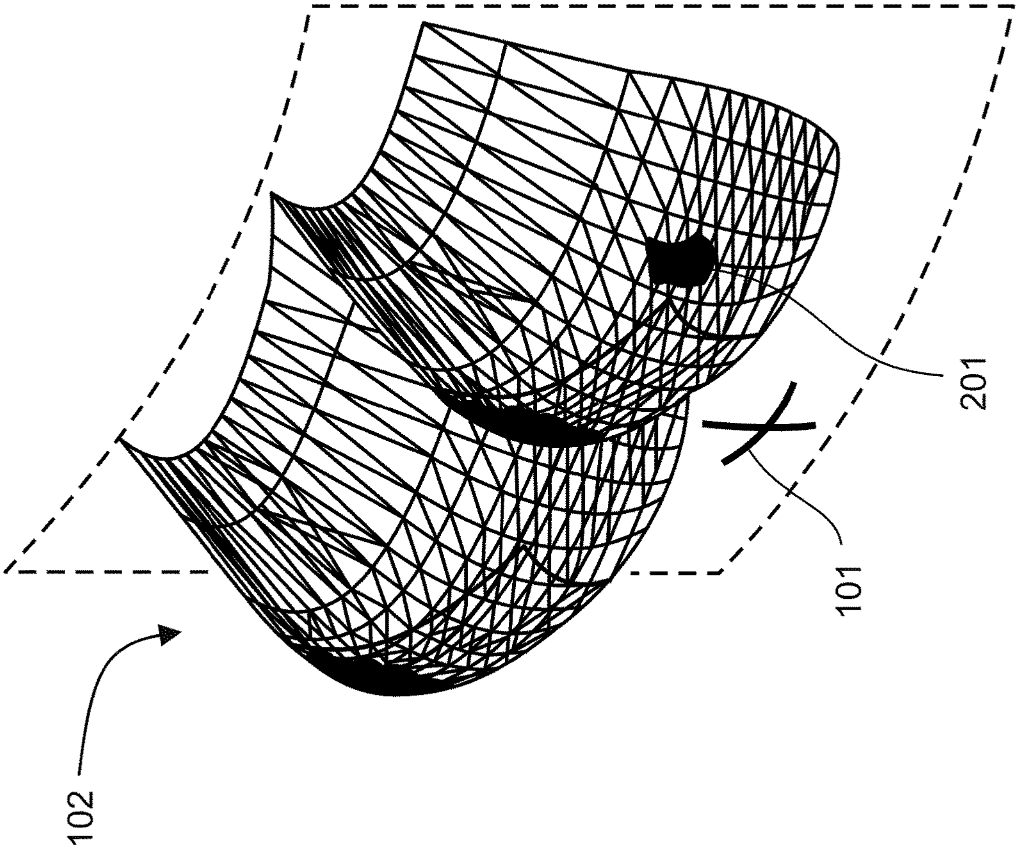
Figure 2:
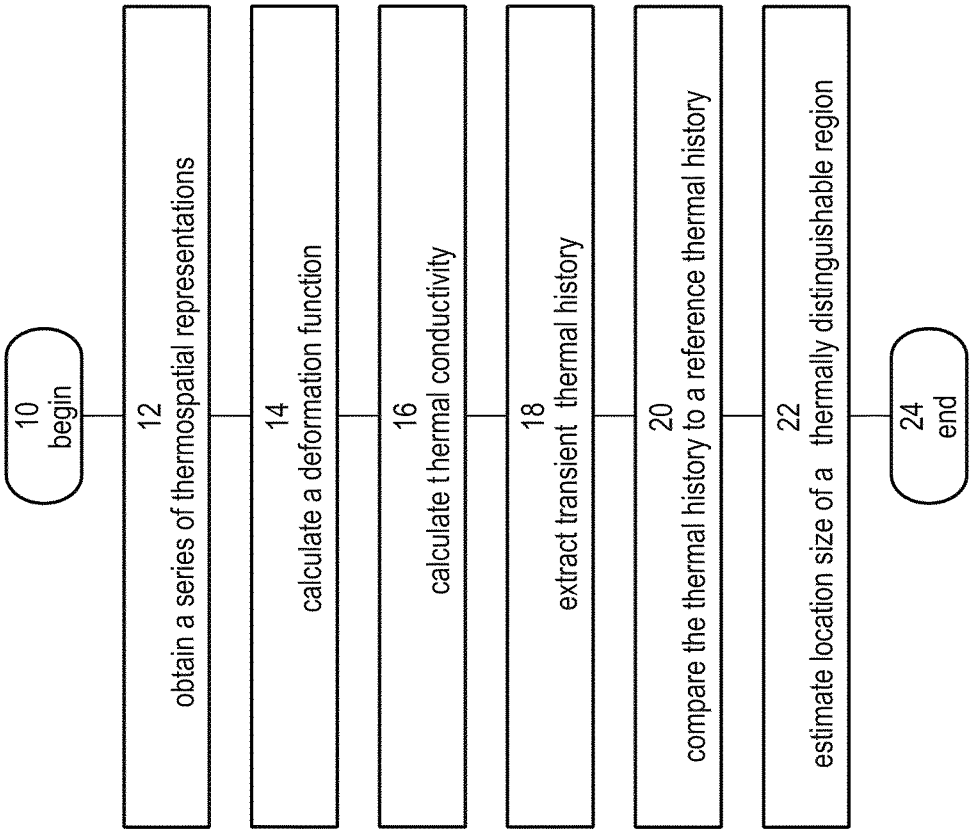
Figure 3:
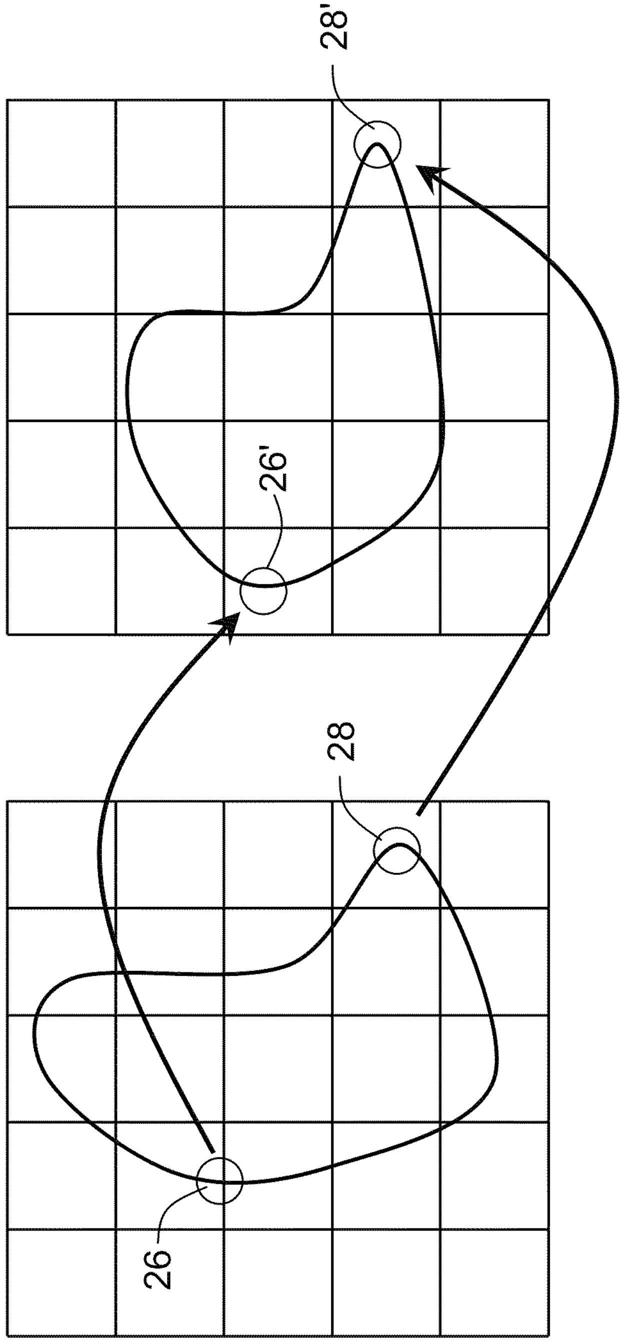
Figure 4:
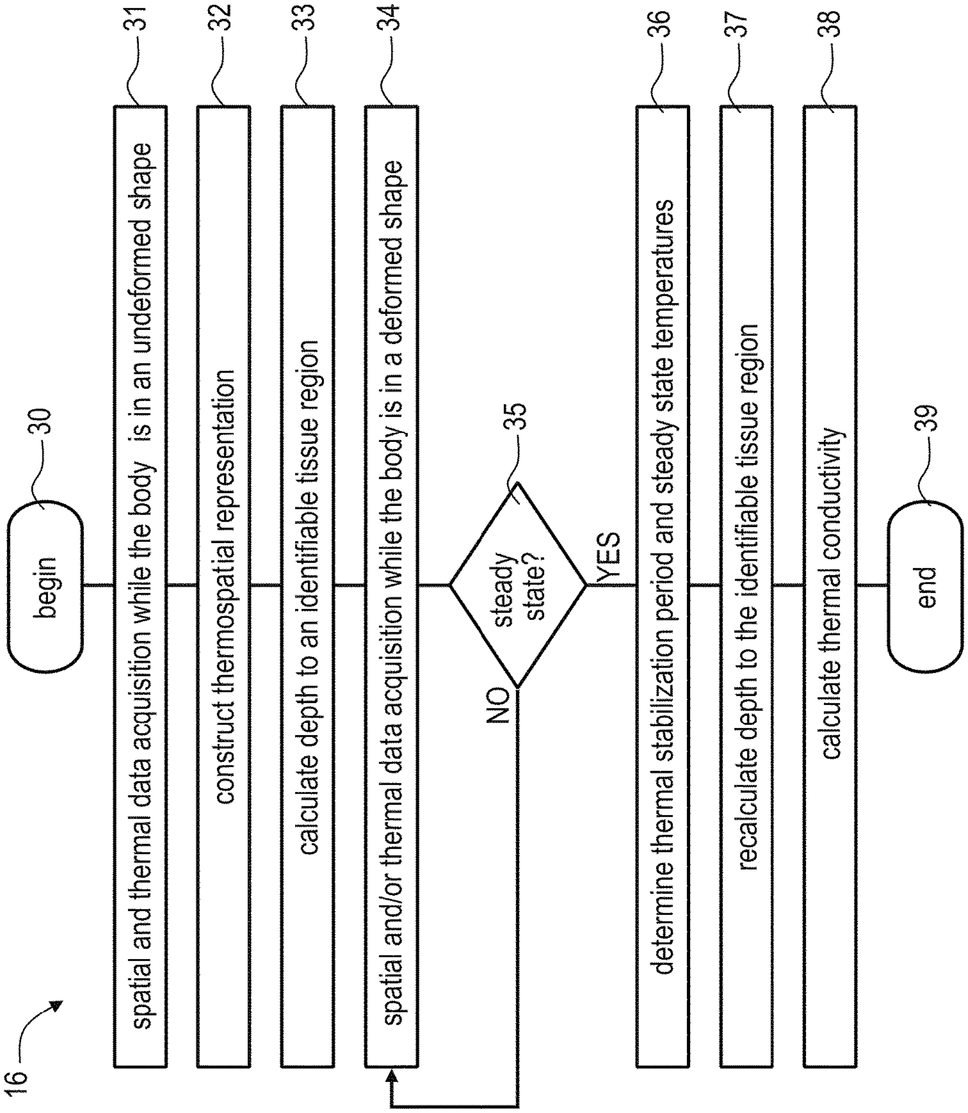
Figure 5A:
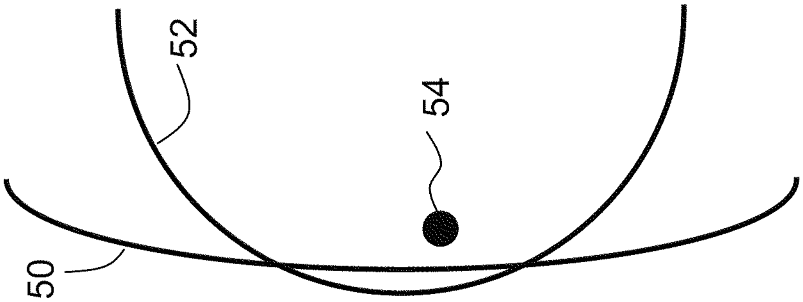
Figure 5B:
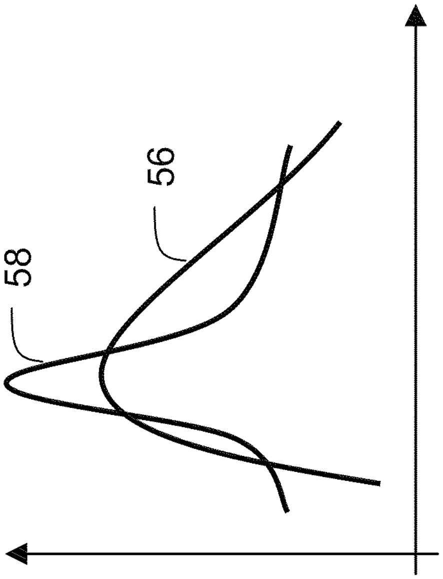
Figure 6A:
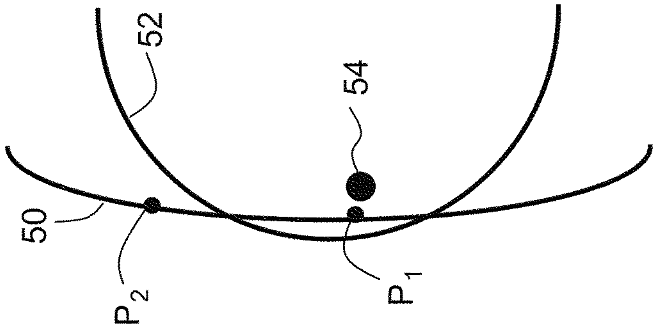
Figure 6B:
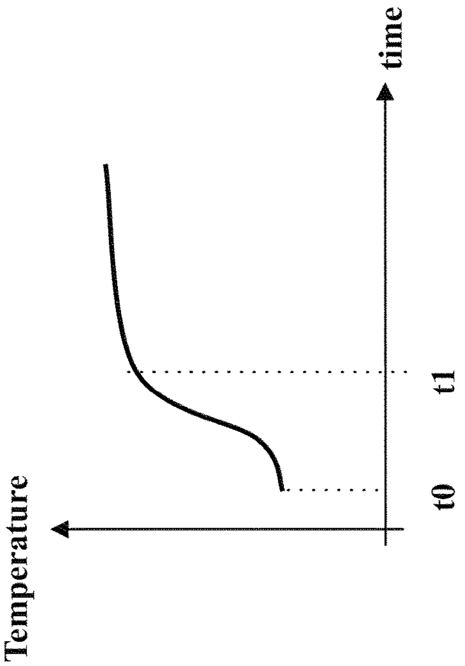
Figure 6C:
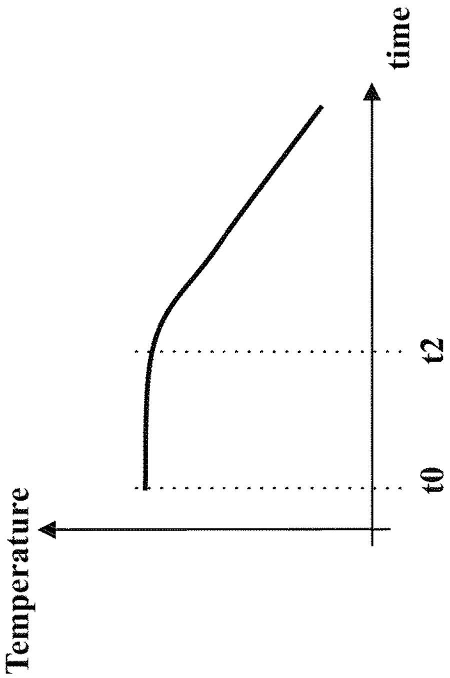
Figure 7:
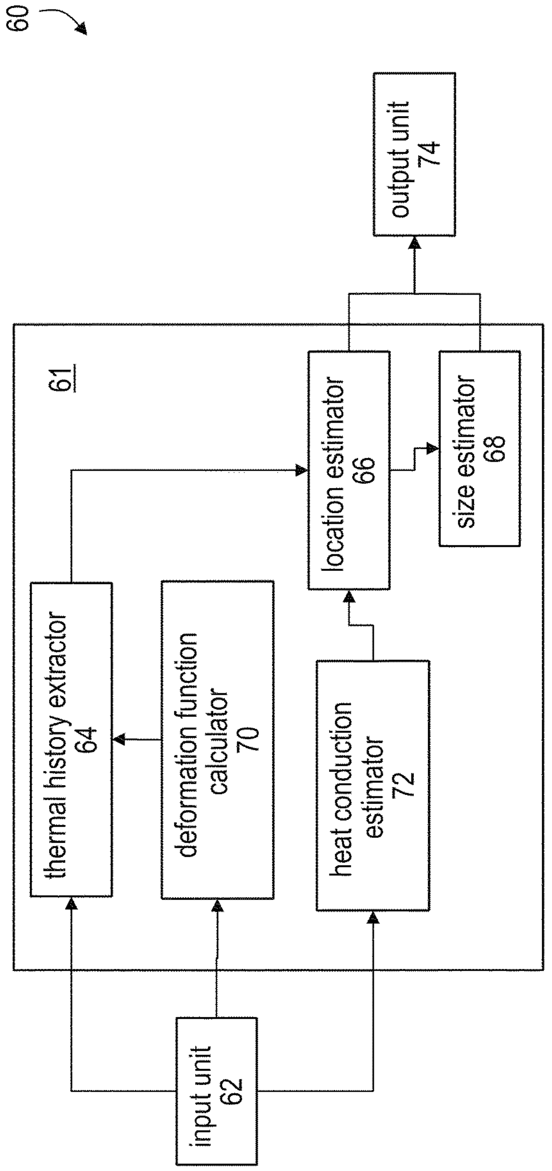
Figure 8:
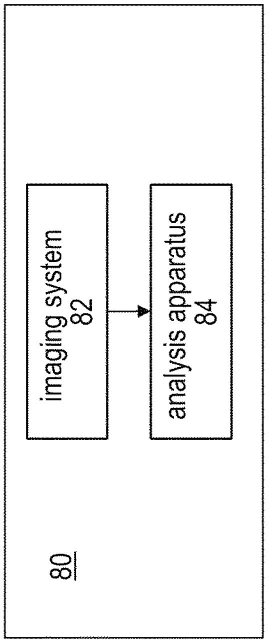
Figures 11A, 11B, 11C, 11D:
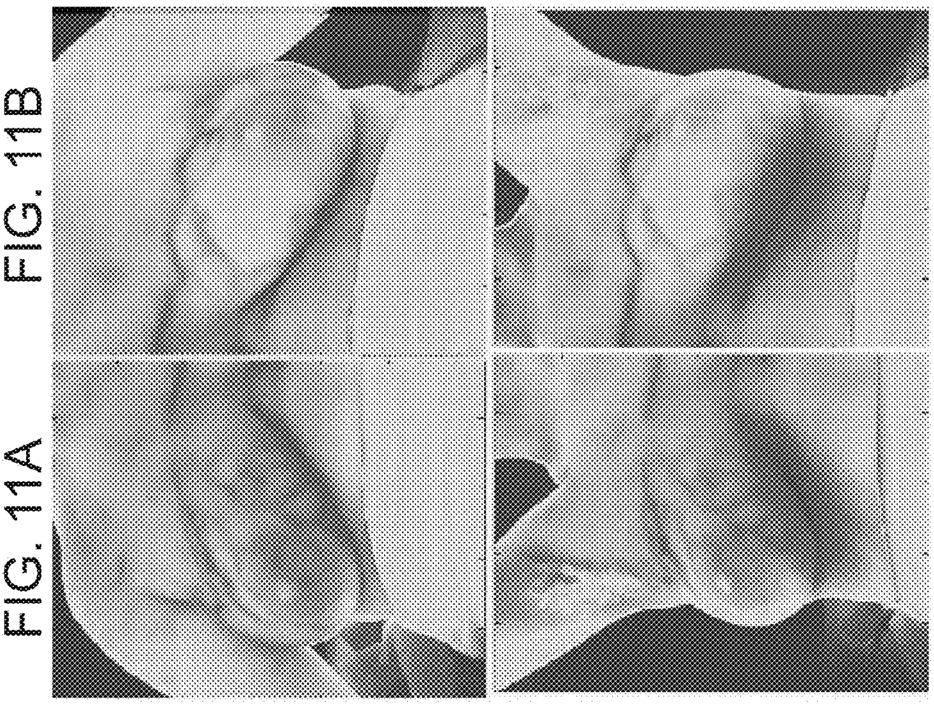

FIGS. 1A-C are schematic illustrations of a thermospatial representation, according to some embodiments of the present invention;

FIG. 2 is a flowchart diagram of a method suitable for analyzing thermal data, according to various exemplary embodiments of the present invention;

FIG. 3 is a schematic illustrations of a deformation function, according to various exemplary embodiments of the present invention;

FIG. 4 is a flowchart diagram of a calibration procedure, according to various exemplary embodiments of the present invention;

FIGS. 5A-B are schematic illustrations showing two shapes of a body section and two corresponding profiles of heat signals, according to various exemplary embodiments of the present invention;

FIGS. 6A-C are schematic illustrations showing two shapes of a body section and two heat signals as a function of the time as measured at two points on the surface of the body section;

FIG. 7 is a schematic illustration of an apparatus for analyzing thermal data, according to various exemplary embodiments of the present invention;

FIG. 8 is a schematic illustration of an imaging and processing system, according to some embodiments of the present invention;

FIGS. 9A-F and 10A-E are schematic illustration of a thermospatial imaging system, according to various exemplary embodiments of the present invention;

FIGS. 11A-D are thermal images of a right breast (FIGS. 11A and 11C) and a left breast (FIGS. 11B and 11D) of a female subject standing with her hands at the side of her body (FIGS. 11A-B) and with her hands overhead (FIGS. 11C-D).

DESCRIPTION OF SPECIFIC EMBODIMENTS OF THE INVENTION

The present invention, in some embodiments thereof, relates to thermal images and, more particularly, but not exclusively, to the analysis of thermal images.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors have devised an approach which enables the analysis of thermal data, e.g., for the purpose of determining presence location and/or size of a thermally distinguishable region. When the thermal data is acquired from a body section such as a breast of a woman, the analysis of the present embodiments can be used to extract properties of the underlying tissue.

For example, determination of the presence, location and/or size of a tumor which is a thermally distinguished from healthy tissue. An elevated temperature is generally associated with a tumor due to the metabolic abnormality of the tumor and proliferation of blood vessels (angiogenesis) at and/or near the tumor. In a cancerous tumor the cells double faster and thus are more active and generate more heat. This tends to enhance the temperature differential between the tumor itself and the surrounding temperature. The present embodiments can therefore be used for diagnosis of cancer, particularly, but not exclusively breast cancer.

The analysis according to some embodiments of the present invention is based on surface information, which is obtained or captured from the surface of the body section, and which includes spatial information as well as thermal information.

The spatial information comprises data pertaining to geometric properties of a non-planar surface which at least partially encloses a three-dimensional volume. Generally, the non-planar surface is a two-dimensional object embedded in a three-dimensional space. Formally, a non-planar surface is a metric space induced by a smooth connected and compact Riemannian 2-manifold. Ideally, the geometric properties of the non-planar surface would be provided explicitly for example, the slope and curvature (or even other spatial derivatives or combinations thereof) for every point of the non-planar surface. Yet, such information is rarely attainable and the spatial information is provided for a sampled version of the non-planar surface, which is a set of points on the Riemannian 2-manifold and which is sufficient for describing the topology of the 2-manifold. Typically, the spatial information of the non-planar surface is a reduced version of a 3D spatial representation, which may be either a point-cloud or a 3D reconstruction (e.g., a polygonal mesh or a curvilinear mesh) based on the point cloud. The 3D spatial representation is expressed via a 3D coordinate system, such as, but not limited to, Cartesian, Spherical, Ellipsoidal, 3D Parabolic or Paraboloidal coordinate 3D system.

The term "surface" is used herein as an abbreviation of the term "non-planar surface".

The spatial data, in some embodiments of the present invention, can be in a form of an image. Since the spatial data represent the surface, such an image is typically a two-dimensional image which, in addition to indicating the lateral extent of body members, further indicates the relative or absolute distance of the body members, or portions thereof, from some reference point, such as the location of the imaging device. Thus, the image typically includes information residing on a non-planar surface of a three-dimensional body and not necessarily in the bulk. Yet, it is commonly acceptable to refer to such image as "a three-dimensional image" because the non-planar surface is conveniently defined over a three-dimensional system of coordinate. Thus, throughout this specification and in the claims section that follows, the terms "three-dimensional image" and "three-dimensional representation" primarily relate to surface entities.

The thermal information comprises data pertaining to heat evacuated from or absorbed by the surface. Since different parts of the surface generally evacuate or absorb different amount of heat, the thermal information comprises a set of tuples, each comprising the coordinates of a region or a point on the surface and a thermal numerical value (e.g., temperature, thermal energy) associated with the point or region. The thermal information can be transformed to visible signals, in which case the thermal information is in the form of a thermographic image. The terms "thermographic image" and thermal information are used interchangeably throughout the specification without limiting the scope of the present invention in any way. Specifically, unless otherwise defined, the use of the term "thermographic image" is not to be considered as limited to the transformation of the thermal information into visible signals. For example, a thermographic image can be stored in the memory of a computer readable medium as a set of tuples as described above.

The surface information (thermal and spatial) of a body is typically in the form of a synthesized representation which includes both thermal data representing the thermal image and spatial data representing the surface, where the thermal data is associated with the spatial data (i.e., a tuple of the spatial data is associated with a heat-related value of the thermal data). Such representation is referred to as a thermospatial representation. The thermospatial representation can be in the form of digital data (e.g., a list of tuples associated with digital data describing thermal quantities) or in the form of an image (e.g., a three-dimensional image color-coded or grey-level coded according to the thermal data). A thermospatial representation in the form of an image is referred to hereinafter as a thermospatial image.

The thermospatial image is defined over a 3D spatial representation of the body and has thermal data associated with a surface of the 3D spatial representation, and arranged gridwise over the surface in a plurality of picture-elements (e.g., pixels, arrangements of pixels) each represented by an intensity value or a grey-level over the grid. It is appreciated that the number of different intensity values can be different from the number of grey-levels. For example, an 8-bit display can generate 256 different grey-levels. However, in principle, the number of different intensity values corresponding to thermal information can be much larger. As a representative example, suppose that the thermal information spans over a range of 37° C. and is digitized with a resolution of 0.1° C. In this case, there are 370 different intensity values and the use of grey-levels is less accurate by a factor of approximately 1.4. In some embodiments of the present invention the processing of thermal data is performed using intensity values, and in some embodiments of the present invention the processing of thermal data is performed using grey-levels. Combinations of the two (such as double processing is also contemplated).

The term "pixel" is sometimes abbreviated herein to indicate a picture-element. However, this is not intended to limit the meaning of the term "picture-element" which refers to a unit of the composition of an image.

When the thermospatial representation is in the form of digital data, the digital data describing thermal properties can also be expressed either in terms of intensities or in terms of grey-levels as described above. Digital thermospatial representation can also correspond to thermospatial image whereby each tuple corresponds to a picture-element of the image.

Typically, one or more thermographic images are mapped onto the surface of the 3D spatial representation to form the thermospatial representation. The thermographic image to be mapped onto the surface of the 3D spatial representation preferably comprises thermal data which are expressed over the same coordinate system as the 3D spatial representation. Any type of thermal data can be used. In one embodiment the thermal data comprises absolute temperature values, in another embodiment the thermal data comprises relative temperature values each corresponding, e.g., to a temperature difference between a respective point of the surface and some reference point, in an additional embodiment, the thermal data comprises local temperature differences. Also contemplated, are combinations of the above types of temperature data, for example, the thermal data can comprise both absolute and relative temperature values, and the like.

Typically, but not obligatorily, the information in the thermographic image also includes the thermal conditions (e.g., temperature) at one or more reference markers.

The mapping of the thermographic image onto the surface of the 3D spatial representation is by positioning the reference markers (e.g., by comparing their coordinates in the thermographic image with their coordinates in the 3D spatial representation), to thereby match also other points hence to form the synthesized thermospatial representation.

Optionally and preferably, the mapping of thermographic images is accompanied by a correction procedure in which thermal emissivity considerations are employed.

The thermal emissivity of a body member is a dimensionless quantity defined as the ratio between the amount of thermal radiation emitted from the surface of the body member and the amount of thermal radiation emitted from a black body having the same temperature as the body member. Thus, the thermal emissivity of an idealized black body is 1 and the thermal emissivity of all other bodies is between 0 and 1. It is commonly assumed that the thermal emissivity of a body is generally equal to its thermal absorption factor.

The correction procedure can be performed using estimated thermal characteristics of the body of interest. Specifically, the thermographic image is mapped onto a non-planar surface describing the body taking into account differences in the emissivity of regions on the surface of the body. A region with a different emissivity value compared to its surrounding can be, for example, a scarred region, a pigmented region, a nipple region on the breast, a nevus. Additionally, the emissivity values of subjects with different skin colors may differ.

In some embodiments of the present invention, the thermographic image is weighted according to the different emissivity values of the surface. For example, when information acquired by a thermal imaging device includes temperature or energy values, at least a portion of the temperature or energy values can be divided by the emissivity values of the respective regions on the surface of the body. One of ordinary skill in the art will appreciate that such procedure results in effective temperature or energy values which are higher than the values acquired by the thermal imaging device. Since different regions may be characterized by different emissivity values, the weighted thermographic image provides better estimate regarding the heat emitted from the surface of the body.

A representative example of a synthesized thermospatial image for the case that the body comprise the breasts of a woman is illustrated in FIGS. 1*a-c*, showing a 3D spatial representation illustrated as a non-planar surface (FIG. 1*a*), a thermographic image illustrated as planar isothermal contours (FIG. 1*b*), and a synthesized thermospatial image formed by mapping the thermographic image on a surface of the 3D spatial representation (FIG. 1*c*). As illustrated, the thermal data of the thermospatial image is represented as grey-level values over a grid generally shown at 102. It is to be understood that the representation according to grey-level values is for illustrative purposes and is not to be considered as limiting. As explained above, the processing of thermal data can also be performed using intensity values. Also shown in FIGS. 1*a-c*, is a reference marker 101 which optionally, but not obligatorily, can be used for the mapping.

The 3D spatial representation, thermographic image and synthesized thermospatial image can be obtained in any technique known in the art, such as the technique disclosed in International Patent Publication No. WO 2006/003658, U.S. Published Application No. 20010046316, and U.S. Pat.

Nos. 6,442,419, 6,765,607, 6,965,690, 6,701,081, 6,801,257, 6,201,541, 6,167,151, 6,094,198 and 7,292,719.

Some embodiments of the invention can be embodied on a tangible medium such as a computer for performing the method steps. Some embodiments of the invention can be embodied on a computer readable medium, comprising computer readable instructions for carrying out the method steps. Some embodiments of the invention can also be embodied in electronic device having digital computer capabilities arranged to run the computer program on the tangible medium or execute the instruction on a computer readable medium. Computer programs implementing method steps of the present embodiments can commonly be distributed to users on a tangible distribution medium. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

FIG. 2 is a flowchart diagram of a method suitable for analyzing thermal data, according to various exemplary embodiments of the present invention. It is to be understood that, unless otherwise defined, method steps described hereinbelow can be executed either contemporaneously or sequentially in many combinations or orders of execution. Specifically, the ordering of the flowchart diagrams is not to be considered as limiting. For example, two or more method steps, appearing in the following description or in the flowchart diagrams in a particular order, can be executed in a different order (e.g., a reverse order) or substantially contemporaneously. Additionally, several method steps described below are optional and may not be executed.

The method begins at step 10 and continues to step 12 in which a series of thermospatial representation of a section of a living body is obtained. Each thermospatial representation of the series includes thermal data representing a thermal image of the body section and spatial data representing a non-planar surface of the body section, where the thermal data is associated with the spatial data.

Different thermospatial representations of the series include thermal data acquired from the body section at different time instants. Optionally, different thermospatial representations of the series include spatial data acquired from the body section at different time instants. Such series of thermospatial representations is used by the method of the present embodiments to determine thermal and optionally spatial changes occurred in the body section over time.

The series can include any number of thermospatial representations. It was found by the inventors of the present invention that two thermospatial representations are sufficient to perform the analysis, but more than two thermospatial representations (e.g., 3, 4, 5 or more) can also be used, for example, to increase accuracy of the results and/or to allow selection of best acquisitions.

The thermospatial representations of the series can be generated by the method or it can be generated by another method or system from which the thermospatial representations can be serially read by the method. Techniques for generating thermospatial representations are disclosed in International Patent Publication No. WO 2006/003658, U.S. Published Application No. 20010046316, and U.S. Pat. Nos. 6,442,419, 6,765,607, 6,965,690, 6,701,081, 6,801,257, 6,201,541, 6,167,151, 6,094,198 and 7,292,719, the contents of which are hereby incorporated by reference.

Generally, acquisitions of the thermal and spatial data can be performed while the body is in a transient or steady thermal condition.

The term "steady thermal condition" or "steady thermal state" as used herein refer to a thermal state of a body section in which there is no point over the entire surface of the body section for which temporal variations in the temperature are higher than 0.5° C. per minute.

The term "transient thermal condition" or "transient thermal state" as used herein refer to a thermal state of a body section other than a steady thermal state. More preferably, in a transient thermal condition or a transient thermal state there is at least one point over the surface of the body section for which temporal variations in the temperature are higher than 0.5° C. per minute.

Since the series includes more than one thermospatial representation, some acquisitions can be performed while the body is in a transient thermal condition and other acquisitions can be performed while the body is in a steady thermal condition. Yet, in various exemplary embodiments of the present invention the body section is in a transient thermal condition between successive acquisitions of the thermal and spatial data.

In one embodiment, for example, one acquisition of thermal and spatial data can be performed while the body is in a first steady thermal state, and subsequent acquisition of thermal and spatial data can be performed while the body is in a second steady thermal state which differs from the first steady thermal state. In another embodiment, a first acquisition can be performed while the body is in a first steady thermal state, a second acquisition can be performed while the body is in a first transient thermal state, and a third acquisition can be performed while the body is in a second steady thermal state which differs from the first steady thermal state. Also contemplated are embodiments in which all acquisitions are performed while the body is in a transient thermal state, and embodiments in which all acquisitions are performed while the body is in a steady thermal state.

A transient thermal condition of the body section between and optionally during acquisitions of thermal and spatial data can be ensured in more than one way.

In some embodiments of the present invention, the ambient temperature at the surface of the body section is changed between two successive captures of surface information. A change in the ambient temperature corresponds to different boundary conditions for different thermospatial representations. Specifically, in these embodiments, two successive thermospatial representations describe the body section while the subject is exposed to two different ambient temperatures. A change in the ambient temperature can be imposed, for example, by establishing contact between a cold object and the body section or directing a flow of cold gas (e.g., air) to the surface of the body section between successive data acquisitions. Also contemplated is a procedure in which the body section is immersed in cold liquid (e.g., water) between successive data acquisitions. Also contemplated is a procedure in which another body section is exposed to a different (e.g., lower) temperature so as to ensure transient thermal condition. For example, the subject can immerse his or her limb in a cold liquid (e.g., water).

In some embodiments of the present invention, two or more of the thermospatial representations of the series describe the body section while having two or more different shapes. This is typically accomplished by changing the posture of the subject between successive data acquisitions. The change of subject's posture is preferably such that the shape of the body section of interest is deformed. For example, when the body section is a breast of a woman subject, in one posture the woman can stand with her hands at the side of her body and in another posture the woman can stand with her hands overhead, stand with her hands extended in front at shoulder height, bend forwards, lie in prone position and the like. These exemplified postures correspond to different breast shapes.

Change of posture results in transient thermal condition due to a deformation in the thermal path between the thermally distinguished region and other tissue regions. Specifically, upon a posture change, some body tissues move closer to the thermally distinguished region and the thermal path between these tissues and the thermally distinguished region shortens. Conversely, other body tissues move farther from the thermally distinguished region and the thermal path between these tissues and the thermally distinguished region lengthens. Since the length of the thermal path affects the amount of heat transferred over this path, shortening or lengthening of the thermal path results change in heat transfer. When the body of the subject contains, for example, a tumor having elevated temperature, change of posture effects temperature increment for tissues which move closer to the tumor and temperature decrement for tissues which move farther from the tumor.

FIGS. 11*a*-*d* are thermal images of a right breast (FIGS. 11*a* and 11*c*) and a left breast (FIGS. 11*b* and 11*d*) of a female subject standing with her hands at the side of her body (FIGS. 11*a*-*b*) and with her hands overhead (FIGS. 11*c*-*d*). As shown, the change in posture results in a change in the shape of the breasts and a change in the thermal state of their surfaces. The surfaces of breasts were therefore in a transient thermal condition while and immediately after the change in posture.

When the body section is deformed between two acquisitions, the thermal and spatial data are optionally acquired such that the thermospatial representations are alignable with respect to a predetermined fixed reference point on the body. For example, the reference point can be a mark on the arm-pit.

In some embodiments of the present invention the method continues to step 14 in which a deformation function which maps one shape of the body section to another shape thereof is calculated. These embodiments are particularly useful when the body section is deformed between two successive acquisitions. The deformation function generally includes spatial information which describes how picture-elements (e.g., pixels, group of pixels, spots) are transformed under shape deformation. The deformation function can include surface information or volume information as desired. When the deformation function includes surface information the mapping is between points on the surface of the body section before the deformation and points on the surface of the body section after the deformation. When the deformation function includes volume information, the mapping is between points in the body section and on its surface before the deformation and points in the body section on its surface of after the deformation.

Ideally, a deformation function provides mapping pixel-wise between two thermospatial representations. In such ideal case applying the deformation function to the location of each pixel in the thermospatial representation before the deformation creates the spatial information of the thermospatial representation after the deformation. Yet, it was found by the present inventors that it is sufficient to calculate mapping for several picture-elements (e.g., pixels, group of pixels, spots) rather than for each and every pixel of the thermospatial representations. In any event, when step 14 of the method is executed, the deformation function maps between at least one picture-element in the body section before deformation and at least one picture-element in the body section after deformation.

The calculated deformation function is typically in the form of a mapping table in which each entry corresponds to the mapping between two corresponding picture-elements, one being part of the shape before deformation and the other being part of the deformed shape. The calculation of the deformation function can be using any technique known in the art. A representative example includes, without limitation, a finite element method in which the deformation function is approximated as piecewise smooth between discrete elements. The elements can be of arbitrary shape and they typically share nodes and faces with adjacent elements and form at least part of the shape of the body section.

An illustrative example of a deformation function is provided in FIG. 3 showing a first shape (left) and a second shape (right) where the second shape is deformed with respect to the first shape. For clarity of presentation, the shapes are illustrated as planar shapes on a rectangular grid. It is to be understood, however, that it is not intended to exclude non-planar shapes and curved or other non-rectangular grids from the scope of the present invention. The deformation function is represented in FIG. 3 as an arrow, mapping spots 28, 26 in the first shape to their corresponding spots 28', 26' in the second shape. Although FIG. 3 illustrates the mapping of two spots, this need not necessarily be the case, since the mapping can be employed to any number of picture-elements (including a mapping of a single picture-element in the first shape to its corresponding picture-element in the deformed shape).

In some embodiments of the present invention the method continues to step 16 in which a characteristic heat conduction of the body section is estimated based on the series of thermospatial representations. Characteristic heat conduction can be estimated by performing a calibration procedure in which the depth of one or more identifiable tissue regions is known or calculated and the rate of heat transfer to or from the identifiable tissue regions is measured. In various exemplary embodiments of the invention the identifiable tissue regions are sections of blood vessels. It was found by the inventor of the present invention that blood vessel sections can be identified from thermal data with to a relatively high confidence level, and that these blood vessel sections can be used for estimating the thermal conductivity.

For example, in some embodiments of the present invention step 16 is executed by performing the following calibration procedure (see FIG. 4).

The procedure begins at 30 and continues to 31 at which a first data acquisition is performed while the body section is in a first shape referred to hereinafter as the "undeformed shape." The procedure continues to 32 at which a first thermospatial representation is constructed, and 33 at which the depth of an identifiable tissue region is calculated using the first thermospatial representation. The identifiable tissue region can be for example, a distinguishable blood vessel section. Calculation of depth from the thermospatial representation can be done, for example, by triangulation or any other technique known in the art.

The procedure subsequently proceeds to 34 in which a second data acquisition is performed while the body section is in a second shape which is deformed with respect to the undeformed shape. A second thermospatial representation is then constructed. While the shape is still deformed, data is repeatedly acquired until the identifiable tissue region is in a steady thermal state (decision 35). The repetition of data acquisition (process 34) can be done only for thermal data since there is no change in the shape of the body section between successive acquisitions.

The procedure continues to 36 at which the thermal stabilization period is determined. Generally, the thermal stabilization period can be defined as the elapsed time between the deformation of the body shape and the onset of steady state. The procedure can also calculate the difference in steady state temperatures before and after deformation. The procedure proceeds to 37 in which the second thermospatial representation is used for recalculating the depth of the same identifiable tissue region so as to determine the difference in the depths due to the deformation. The procedure then continues to 38 at which the thermal conductivity is calculated based on the knowledge of the thermal stabilization period and the differences in depths and steady state temperatures. To this end, the Stefan-Boltzmann law can be used to approximate heat flux.

The procedure ends at 39.

Referring again to the flowchart diagram of FIG. 2, the method continues to step 18 in which transient thermal history of the body section is extracted, based on thermal variations among the series of thermospatial representations. The transient thermal history includes temporal variation of local thermal quantities over at least part of the surface of the body section. The local thermal quantities can be for example temperatures, intensity values or grey-levels as individually measured at one or more surface locations. The temperatures, intensity values or grey-levels can be absolute or they can be relative to other surface locations.

The variations in local thermal quantities can be extracted for any number of picture-elements of the thermospatial representations. Typically the method selects a set of picture-elements and extracts temporal variations in the thermal quantities for each picture-element in the set.

The term "set of picture-elements" encompass a plurality of picture-elements as well as a single picture-element. In some embodiments of the present invention the set of picture-elements includes all the picture-elements of the thermospatial representation.

In embodiments in which a deformation function is calculated, the deformation function is utilized for determining a correspondence between sets of picture-element belonging to different thermospatial representations of the series to allow determination of individual thermal variation for each picture-element in the set.

For each picture-element of the set, the temporal variations can be defined in a binary manner (e.g., whether the picture-element exhibits an increment or a decrement in temperature due to the transient thermal condition), or by value (e.g., the change or rate of change in temperature exhibited by the picture-element due to the transient thermal condition). For one or more picture-elements, the transient thermal history can optionally be expressed in terms of thermal stabilization period (onset of a steady thermal state at the picture-element) or thermal response delay (onset of temperature change at the picture-element). Also contemplated are embodiments in which more than one type of temporal variation is extracted for each picture-element of the set. It was found by the present inventor that the use of two or more types of temporal variation for each picture-element is advantageous from the standpoint of accuracy and specificity. Yet, the use of one type of temporal variation is not excluded from the scope of the present invention.

In various exemplary embodiments of the invention the method proceeds to step 20 in which the transient thermal history is compared to a reference transient thermal history. Typically, but not obligatorily, the reference thermal history represents a situation in which no thermally distinguishable region is present.

The reference thermal history generally corresponds to a thermal history as extracted from a series of reference thermospatial representations, which can be obtained from a library or can be constructed by the method of the present embodiments. The reference thermospatial representation can describe a reference body section other than the body section being analyzed. Typically, the reference body section is a body section which is similar in shape to the body section being analyzed. For example, when the body section is a breast of a woman, the reference body section can be the other breast of the same woman. Preferably, but not obligatorily, the reference body section is devoid of thermally distinguishable region.

The comparison between thermal histories can be used for determining the likelihood for the presence of a thermally distinguishable region in the body section. Generally, when the distribution of the transient thermal variations over the surface of the reference body section, is considerably different from the distribution of the transient thermal variations over the surface of the body section being analyzed, the method can determine that it is likely that a thermally distinguishable region is present. For example, when the transient thermal variations are distributed generally uniformly over the surface of the reference body section, but exhibit a considerable local nature over the surface of the body section being analyzed, the method can determine that it is likely that a thermally distinguishable region is present.

This can be better understood from the following non-limiting example. Suppose that the reference body section has a similar shape to the body section of interest such that there is a geometrical correspondence between a set S of points on the surface of the body section of interest and a set $S_R$ of points on the surface of the reference body section. Suppose further that $P_1 \in S$ and $P_2 \in S$ correspond to $Q_1 \in S_R$ and $Q_2 \in S_R$, respectively, and that the method determines the temporal derivative (transient temperature change) $\partial t/\partial T$ at each of points $P_1$, $P_2$, $Q_1$ and $Q_2$. In some embodiments of the present invention if the ratio $(\partial T(P_1)/\partial_t)/(\partial T(P_2)/\partial t)$ is substantially different (say, by more than 10%) from the ratio $(\partial T(Q_1)/\partial_t)/(\partial T(Q_2)/\partial t)$, the method determines that it is likely that a thermally distinguishable region is present. If, on the other hand the above ratios are similar (say, within 10%) the method determines that it is not likely that a thermally distinguishable region is present. The likelihood can also be quantified (e.g., expressed as percentage) based on the difference or ratio between the above ratios.

The method continues to step 22 in which the transient thermal history information is used to estimate a location of an internal thermally distinguishable region in body section.

Generally, the location of the internal thermally distinguishable region is estimated by analyzing the differences between the thermospatial representations in the series. FIG. 5*a* is a schematic illustration of an undeformed shape 52 and a deformed shape 50. Also shown in FIG. 5*a* is a thermally distinguishable region 54 having an elevated temperature relative to its surrounding tissues. FIG. 5*b* illustrates the spatial profile of two heat signals 56 and 58, where signal 56 is acquired while the body is in shape 52 and signal 58 is acquired while the body is in shape 50. As shown, heat signal 58 is narrower than heat signal 56. This is because the location of region 54 is closer to the surface of the body when the body is in shape 50 relative to its location when the body is in shape 52.

FIG. 6*a* illustrates shapes 50 and 52 with two representative points $P_1$ and $P_2$ marked on surface 50, where as a result of the deformation, the thermal path between $P_1$ and region 54 shortened and the thermal path between $P_2$ and region 54 lengthened. FIG. 6*b* is a graph showing the heat signal as measured at $P_1$ as a function of the time, and FIG. 6*c* is a graph showing the heat signal as measured at $P_2$ as a function of the time. As shown, the heat signal at $P_1$ increases with time since in the deformed shape $P_1$ is closer to region 54 hence receives more heat therefrom, and the heat signal at $P_2$ decreases with time since in the deformed shape $P_2$ is farther from region 54 hence receives less heat therefrom. Marked on the time axis of FIG. 6*b* is an instant $t_1$ designating the onset of steady state at $P_1$. The period of time from the deformation time $t_0$ to $t_1$ is referred to herein as "thermal stabilization period." Marked on the time axis of FIG. 6*c* is an instant $t_2$ designating the onset of temperature change at $P_2$. The period of time from the deformation time $t_0$ to $t_2$ is referred to herein as "thermal response delay."

In various exemplary embodiments of the invention the method utilizes the above information for estimating the location of region 54.

In some embodiments of the present invention the method selects a collection of points over the surface and determines, for each point in the collection, whether the temperature at the point remained unchanged, increased or decreased as a result of the transient state. These embodiments are particularly useful when the body section is deformed between two successive acquisitions. Once the direction of change (increment, decrement or none) of change is known, the method can determine for each point in the collection, if the point moved closer to or farther from the thermally distinguishable region. For example, when the thermally distinguishable region has a temperature which is above the temperature of the surrounding tissues, temperature increment at a particular surface point indicates that the surface point has moved closer to the thermally distinguishable region and temperature decrement at a particular surface point indicates that the surface point has moved farther from the thermally distinguishable region, as further detailed hereinunder.

It was found by the present inventor that this information can be utilized to estimate the location of the thermally distinguishable region. Specifically, each point in the collection imposes a constraint that the region is closer or farther (as the case may be) from the point in the deformed shape than in the undeformed shape. Thus, a set of constraints is constructed and the method can search over the thermospatial representation for an internal region satisfying all the constraints.

In some embodiments of the present invention the location of the internal thermally distinguishable region is estimated by determining amount of temperature change for each point of the collection. Specifically, for each point in the collection, the method uses the amount of temperature change to define a quantity which is proportional to the distance between the point and the thermally distinguishable region. For example, when the thermally distinguishable region is a tumor characterized by elevated temperature relative to its neighboring tissues, higher temperature change corresponds to a point being closer to the tumor while lower temperature change corresponds to a point being farther from the tumor. Optionally, the method utilizes the calculated thermal conductivity for defining the quantity.

By defining the quantity for all points in the collection the method acquires sufficient information regarding distance proportions between the points and the thermally distinguishable region. The location of the thermally distinguishable region can then be estimated by searching over the thermospatial representation for an internal region which satisfies all distance proportions.

In some embodiments of the present invention the location of the internal thermally distinguishable region is estimated by determining a temperature change rate for each point in the collection. The temperature change rate is equivalent to a mathematical operation of a first derivative of the temperature with respect to the time. Since such derivative correlates to the length of a thermal path between a surface point and a thermally distinguishable region, the method can use the temperature change rate to define a quantity which is proportional to the distance between the point and the thermally distinguishable region. Once quantities are defined for all points in the collection, the location of the thermally distinguishable region can be estimated as further detailed hereinabove.

In some embodiments of the present invention the location of the internal thermally distinguishable region is estimated by comparing the temperature change rate of one point of the collection to a temperature change rate of another point of the collection. Such procedure allows determining thermal length proportions, whereby a lower temperature change rate indicates a longer thermal length and vice versa. Thermal proportions can be defined between pair of points in the collection or alternatively by selecting a reference point and comparing temperature change rates of all other points in the collection to the temperature change rate of the reference point. Thus, each point in the collection is associated with a thermal length proportion and the method can search over the thermospatial representation for an internal region satisfying all thermal length proportions.

In some embodiments of the present invention, the location of the internal thermally distinguishable region is estimated by determining a thermal stabilization period for each point in the collection. Such a procedure allows defining a quantity which is proportional to the distance between the point and the thermally distinguishable region, whereby a longer thermal stabilization period indicates a shorter distance and vice versa. Similarly to the above embodiment, once quantities are defined for all points in the collection, the location of the thermally distinguishable region can be estimated as further detailed hereinabove. In some embodiments of the present invention, the location of the internal thermally distinguishable region is estimated by comparing the thermal stabilization period of one point in the collection to the thermal stabilization period of another point in the collection, hence to acquire more information.

In some embodiments of the present invention the location of the internal thermally distinguishable region is estimated by determining thermal response delay (elapsed time to the onset of temperature change at the point). Such procedure allows defining a quantity which is proportional to the distance between the point and the thermally distinguishable region, whereby a longer thermal response delay indicates a longer distance and vice versa. Similarly to the above embodiment, once quantities are defined for all points in the collection, the location of the thermally distinguishable region can be estimated as further detailed hereinabove. In some embodiments of the present invention, the location of the internal thermally distinguishable region is estimated by comparing the thermal response delay of one point in the collection to the thermal response delay of another point in the collection, hence to acquire more information.

In some embodiments, as stated, the transient thermal condition is ensured by changing the ambient temperature at the surface of the body of the subject. This can be done irrespectively whether or not the shape of the body section is deformed. When the ambient temperature is changed the location of the thermally distinguishable region can be estimated using principles which are similar to the principles described above. More specifically, a collection of points over the surface is selected and the location of the internal thermally distinguishable region can be estimated by determining a temperature change rate, thermal stabilization period and/or thermal response delay for each point in the collection. Any of these quantities can be used singly or in combination with one or more quantities, and any of these quantities can be used independently for each point and/or exploited for comparison with respective quantities associated with other points of the collection.

When the ambient temperature is changed and the shape of the body section remains substantially undeformed, the deformation function is preferably, but not obligatorily, not calculated, and the estimation of the location of the thermally distinguishable region is based on transient thermal data and static spatial data. It was found by the present Inventor that changes in ambient temperature can provide a sufficiently informative signal for the purpose of estimating the location.

The above embodiments can be employed either singly or in combination or sub-combination.

The method ends at step 24.

Any of the above embodiments can also be utilized for determining the size of the thermally distinguishable region. This can readily be achieved by calculating the number of picture-elements representing the thermally distinguishable region and correlating the number to the volume of the region within the body. The method according to some embodiments of the present invention can thus be utilized for monitoring the evolution of a tumor in a body section. Specifically, selected steps of the method described above can be executed a plurality of times to estimate a size of the tumor at each execution, hence to monitor the evolution of the tumor.

The method according to some embodiments of the present invention can be utilized for treating a tumor in a body section. It these embodiments, selected steps of the method described above are executed so as to estimate the size of the tumor. Subsequently, a destructive treatment is applied to the tumor. The treatment can be radiative or it may include chemotherapy. Following the destructive treatment, selected steps of the method described above are executed again so as to re-estimate the size of the tumor. The destructive treatment can then be repeated until a predetermined criterion is met, which predetermined criterion can be a maximal dosage for the treated subject or tumor size threshold. The tumor size threshold can be expressed in absolute value or as a percentage of the size of the tumor before treatment.

Reference is now made to FIG. 7 which is a schematic illustration of an apparatus 60 for analyzing thermal data, according to various exemplary embodiments of the present invention. Apparatus 60 can be implemented in a computing platform 61, such as a data processor or a computer system and can be used for executing one or more of the method steps described above. Data flow channels between the various components of apparatus 60 are shown as arrows in FIG. 7.

Apparatus 60 comprises an input unit 62 for receiving a series of thermospatial representations describing a section of the living body, and a computing platform 61 which estimates the location or presence of the thermally distinguishable region in the body section. In various exemplary embodiments of the invention apparatus 60 comprises a thermal history extractor 64 configured for extracting transient thermal history of the body section as further detailed hereinabove. In some embodiments of the present invention apparatus 60 comprises a deformation function calculator 70 configured for calculating a deformation function as further detailed hereinabove.

In some embodiments of the present invention apparatus 60 comprises a heat conduction estimator 72 for estimating characteristic heat conduction of body section based on series as further detailed hereinabove.

Apparatus 60 further comprises a location estimator 66 configured for estimating a location of an internal thermally distinguishable region in body section based on transient thermal history, as further detailed hereinabove. In some embodiments of the present invention apparatus 60 comprises a size estimator 68, configured for estimating the size of the internal thermally distinguishable region, as further detailed hereinabove. Apparatus 60 preferably comprises an output unit 74 which issues a report regarding the location and/or size of the thermally distinguishable region.

Reference is now made to FIG. 8 which is a schematic illustration of an imaging and processing system 80, according to some embodiments of the present invention. System 80 comprises a thermospatial imaging system 82 which provides a series of thermospatial representations of the body section, and an analysis apparatus 84 for analyzing the thermospatial representations. The principles and operations of apparatus 84 are similar to the principles and operations of apparatus 60 described above. In some embodiments of the present invention apparatus 84 is apparatus 60.

The following description is of techniques for obtaining the thermospatial representation, according to various exemplary embodiments of the present invention. The techniques described below can be employed by any of the method and apparatus described above.

A thermospatial representation or image can be generally obtained by acquiring one or more thermographic images and mapping the thermographic image(s) on a 3D spatial representation.

Figure 9A:
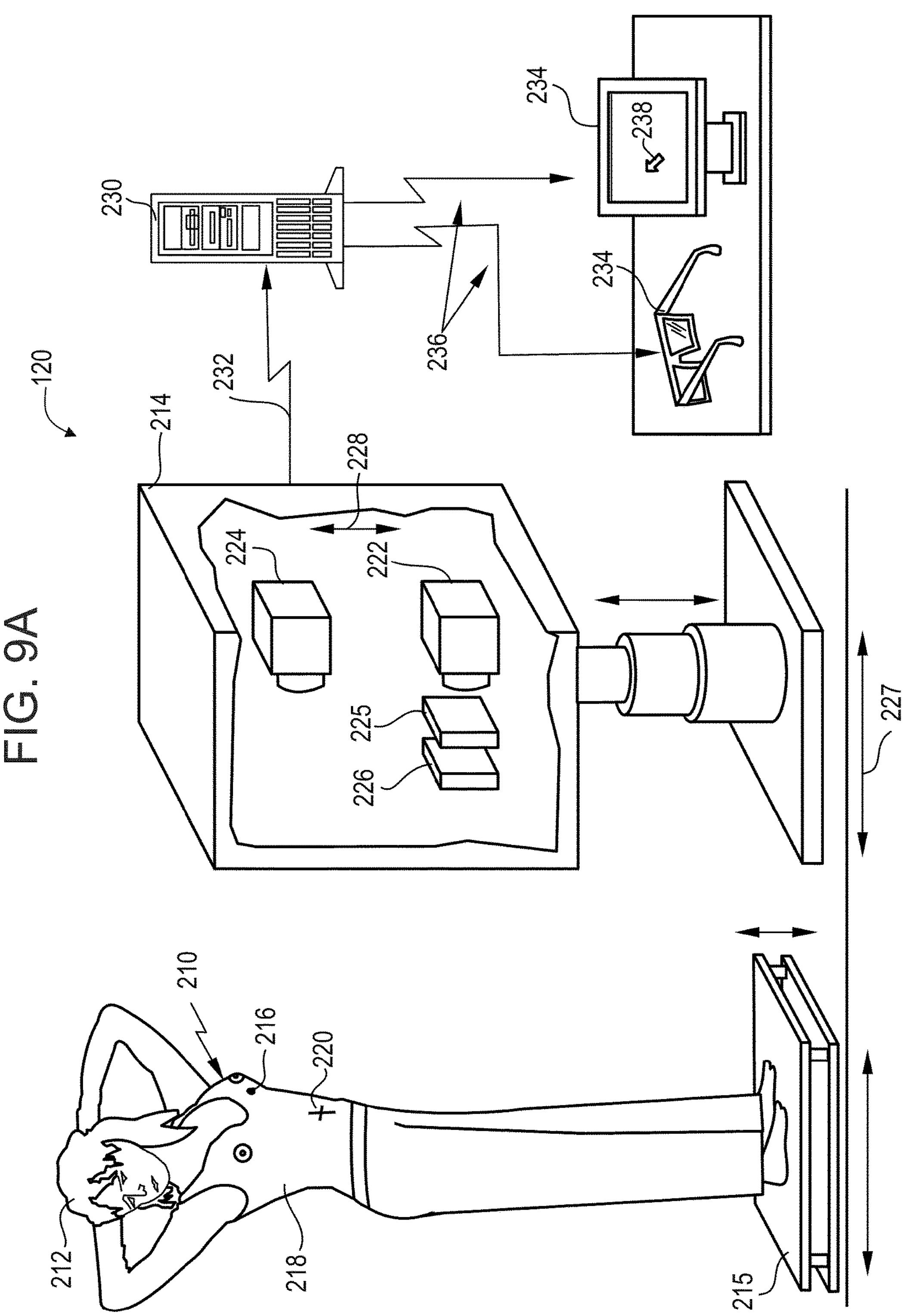

Reference is now made to FIG. 9*a* which is a schematic illustration of a thermospatial imaging system 120 in accordance with preferred embodiments of the present invention. As shown in FIG. 9*a*, a living body 210 or a part thereof of a person 212 is located in front of an imaging device 214. The person 212, may be standing, sitting or in any other suitable position relative to imaging device 214. Person 212 may initially be positioned or later be repositioned relative to imaging device 214 by positioning device 215, which typically comprises a platform moving on a rail, by force of an engine, or by any other suitable force. Additionally, a thermally distinguishable object 216, such as a tumor, may exist in body 210 of person 212. For example, when body 210 comprises a breast, object 216 can be a breast tumor such as a cancerous tumor.

In accordance with a preferred embodiment of the present invention, person 212 may be wearing a clothing garment 218, such as a shirt. Preferably, clothing garment 218 may be non-penetrable or partially penetrable to visible wavelengths such as 400-700 nanometers, and may be penetrable to wavelengths that are longer than visible wavelengths, such as infrared wavelengths. Additionally, a reference mark 220 may be located close to person 212, preferably directly on the body of person 212 and in close proximity to body 210. Optionally and preferably, reference mark 220 is directly attached to body 210. Reference mark 220 may typically comprise a piece of material, a mark drawn on person 212 or any other suitable mark, as described herein below.

Imaging device 214 typically comprises at least one visible light imaging device 222 that can sense at least visible wavelengths and at least one thermographic imaging device 224 which is sensitive to infrared wavelengths, typically in the range of as 3-5 micrometer and/or 8-12 micrometer. Typically imaging devices 222 and 224 are capable of sensing reference mark 220 described hereinabove.

Optionally, a polarizer 225 may be placed in front of visible light imaging device 222. As a further alternative, a color filter 226, which may block at least a portion of the visible wavelengths, may be placed in front of visible light imaging device 222.

Typically, at least one visible light imaging device 222 may comprise a black-and-white or color stills imaging device, or a digital imaging device such as CCD or CMOS. Additionally, at least one visible light imaging device 222 may comprise a plurality of imaging elements, each of which may be a three-dimensional imaging element.

Optionally and preferably, imaging device 214 may be repositioned relative to person 212 by positioning device 227. As a further alternative, each of imaging devices 222 and 224 may also be repositioned relative to person 212 by at least one positioning device 228. Positioning device 227 may comprise an engine, a lever or any other suitable force, and may also comprise a rail for moving imaging device 214 thereon. Preferably, repositioning device 228 may be similarly structured.

Data acquired by visible light imaging device 222 and thermographic imaging device 224 is output to a data processor 230 via a communications network 232, and is typically analyzed and processed by an algorithm running on the data processor. The resulting data may be displayed on at least one display device 234, which is preferably connected to data processor 230 via a communications network 236. Data processor 230 typically comprises a PC, a PDA or any other suitable data processor. Communications networks 232 and 236 typically comprise a physical communications network such as an internet or intranet, or may alternatively comprise a wireless network such as a cellular network, infrared communication network, a radio frequency (RF) communications network, a blue-tooth (BT) communications network or any other suitable communications network.

In accordance with a preferred embodiment of the present invention display 234 typically comprises a screen, such as an LCD screen, a CRT screen or a plasma screen. As a further alternative display 234 may comprise at least one visualizing device comprising two LCDs or two CRTs, located in front of a user's eyes and packaged in a structure similar to that of eye-glasses. Preferably, display 234 also displays a pointer 238, which is typically movable along the X, Y and Z axes of the displayed model and may be used to point to different locations or elements in the displayed data.

Reference is now made to FIGS. 9*b-f* and 10*a-e* which illustrate the various operation principles of thermospatial imaging system 120, in accordance with various exemplary embodiments of the invention.

The visible light imaging is described first, with reference to FIGS. 9*b-f*, and the thermographic imaging is described hereinafter, with reference to FIGS. 10*a-e*. It will be appreciated that the visible light image data acquisition described in FIGS. 9*b-f* may be performed before, after or concurrently with the thermographic image data acquisition described in FIGS. 10*a-e*.

Referring to FIGS. 9*b-f*, person 212 comprising body 210 is located on positioning device 215 in front of imaging device 214, in a first position 240 relative to the imaging device. First image data of body 210 is acquired by visible light imaging device 222, optionally through polarizer 225 or as an alternative option through color filter 226. The advantage of using a color filter is that it can improve the signal-to-noise ratio, for example, when the person is illuminated with a pattern or mark of specific color, the color filter can be used to transmit only the specific color thereby reducing background readings. Additionally, at least second image data of body 210 is acquired by visible light imaging device 222, such that body 210 is positioned in at least a second position 242 relative to imaging device 214. Thus, the first, second and optionally more image data are acquired from at least two different viewpoint of the imaging device relative to body 210.

Figure 9B:
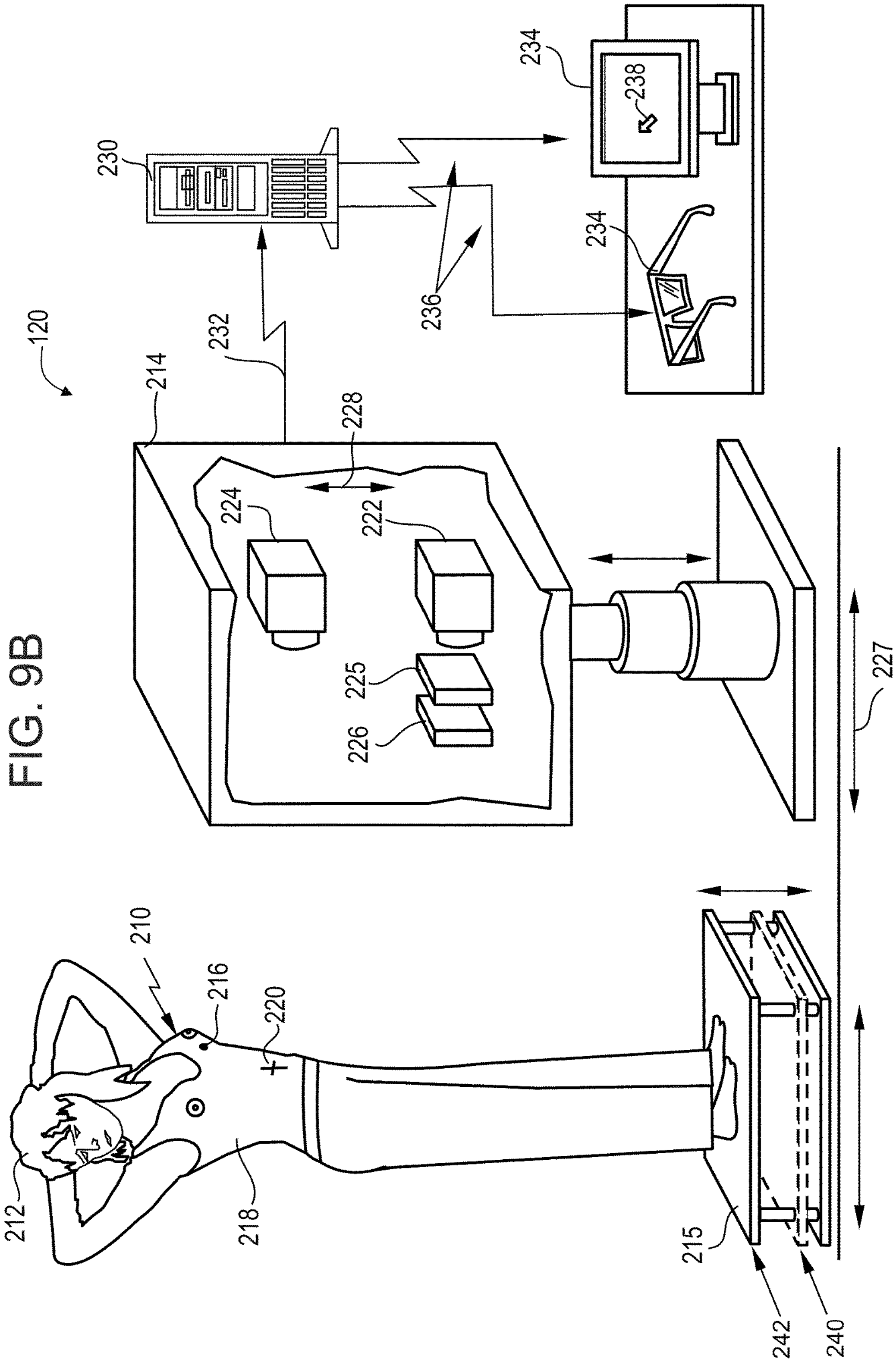
Figure 9C:
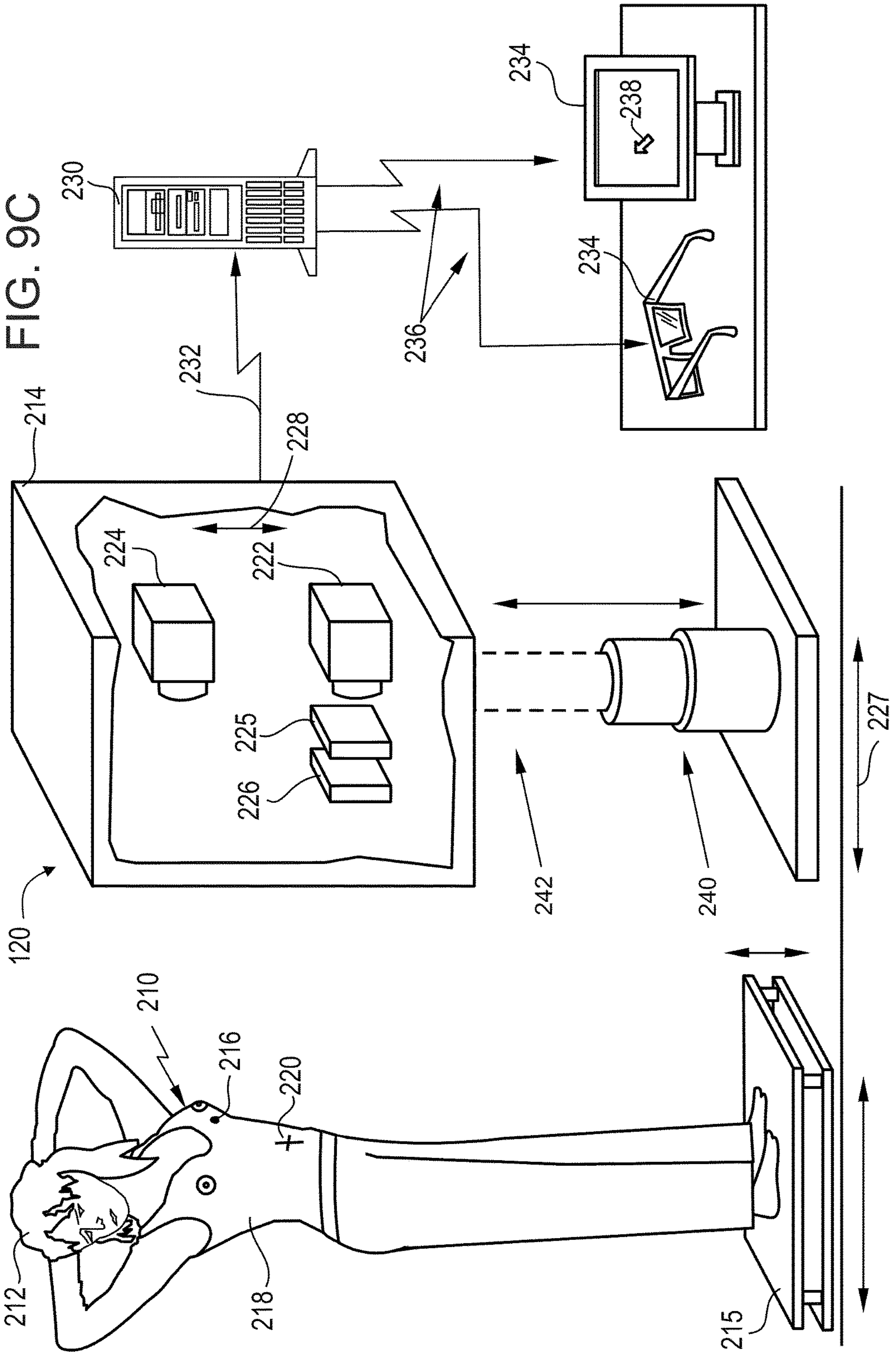
Figure 9D:
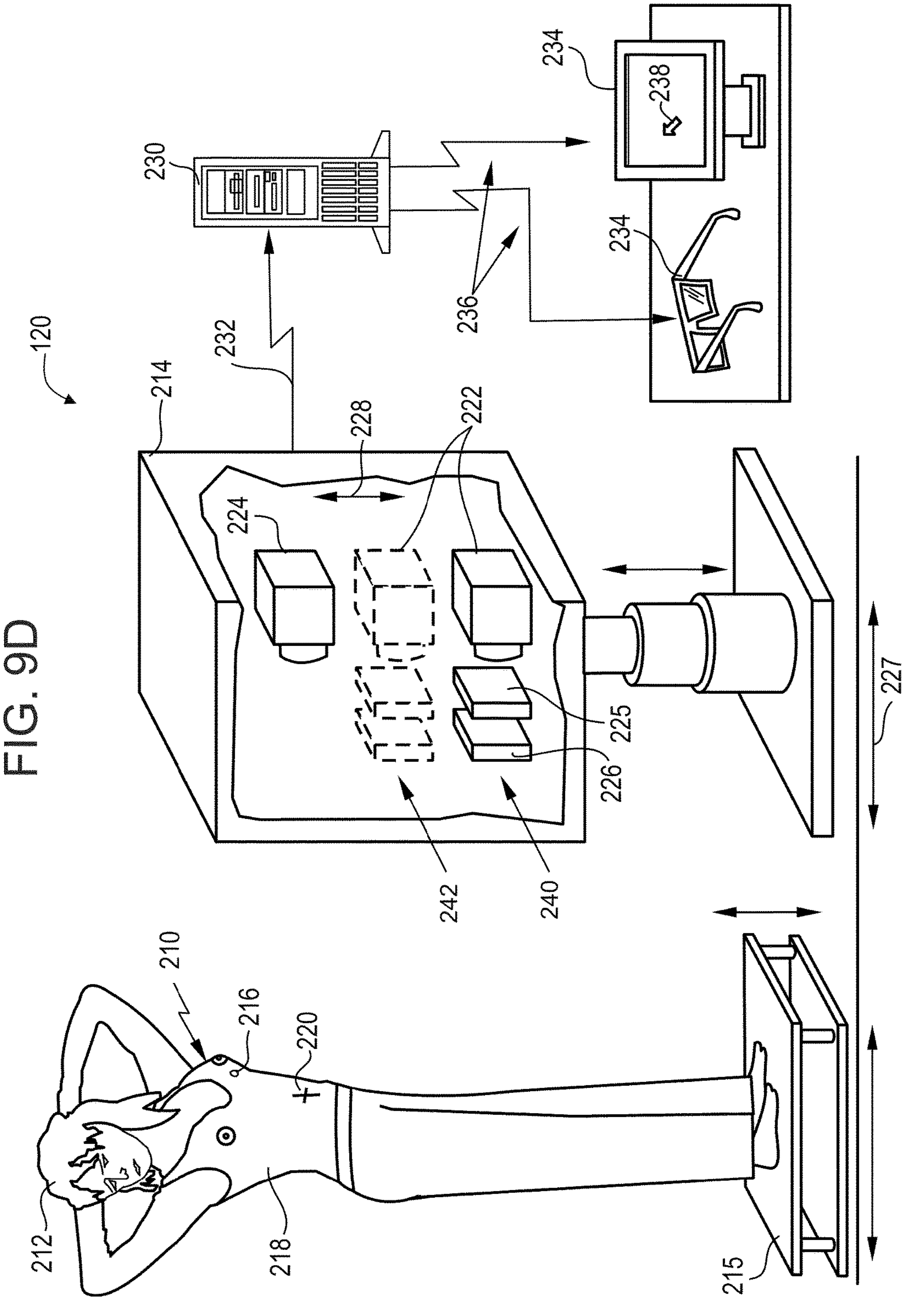
Figure 9E:
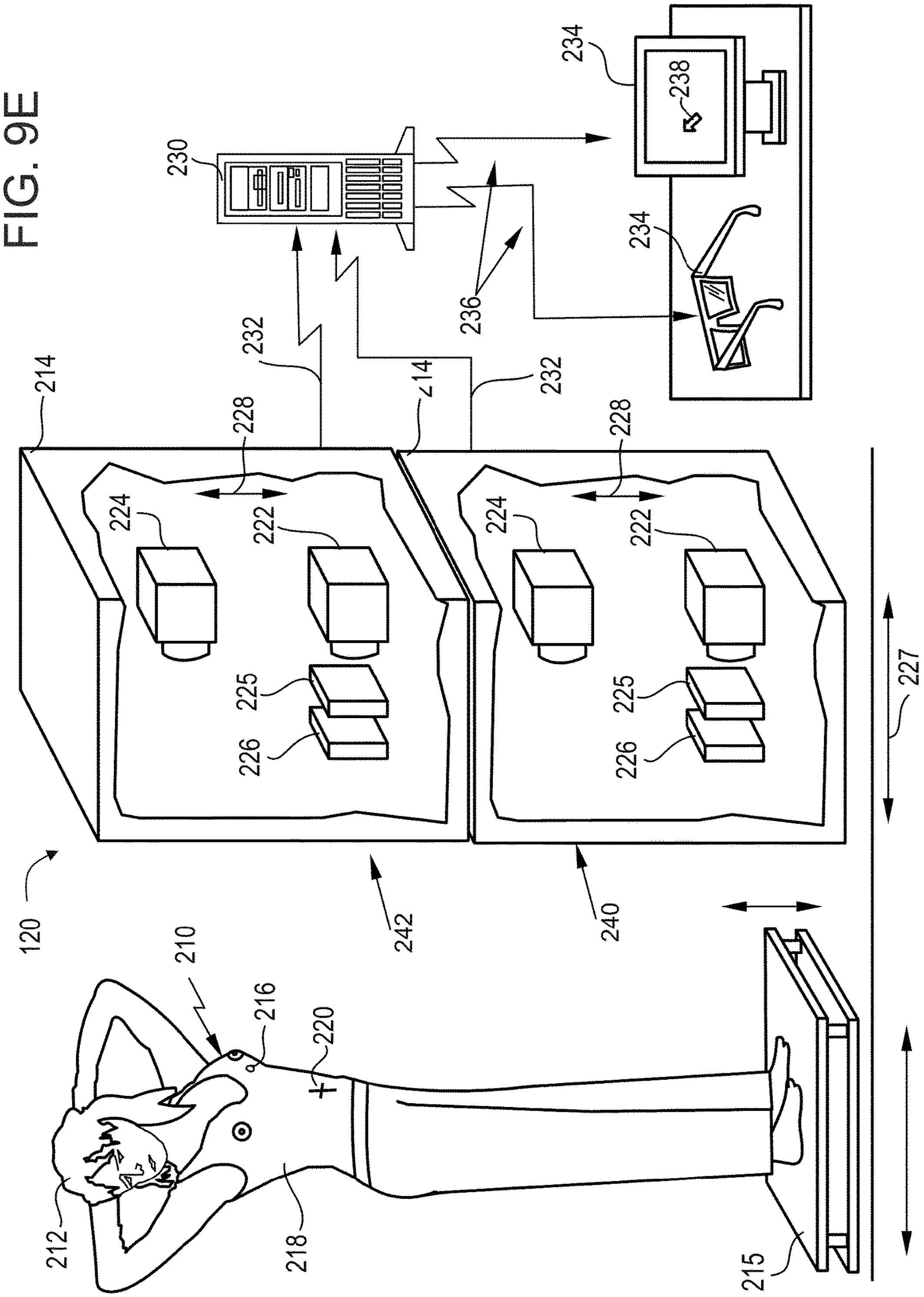
Figure 9F:
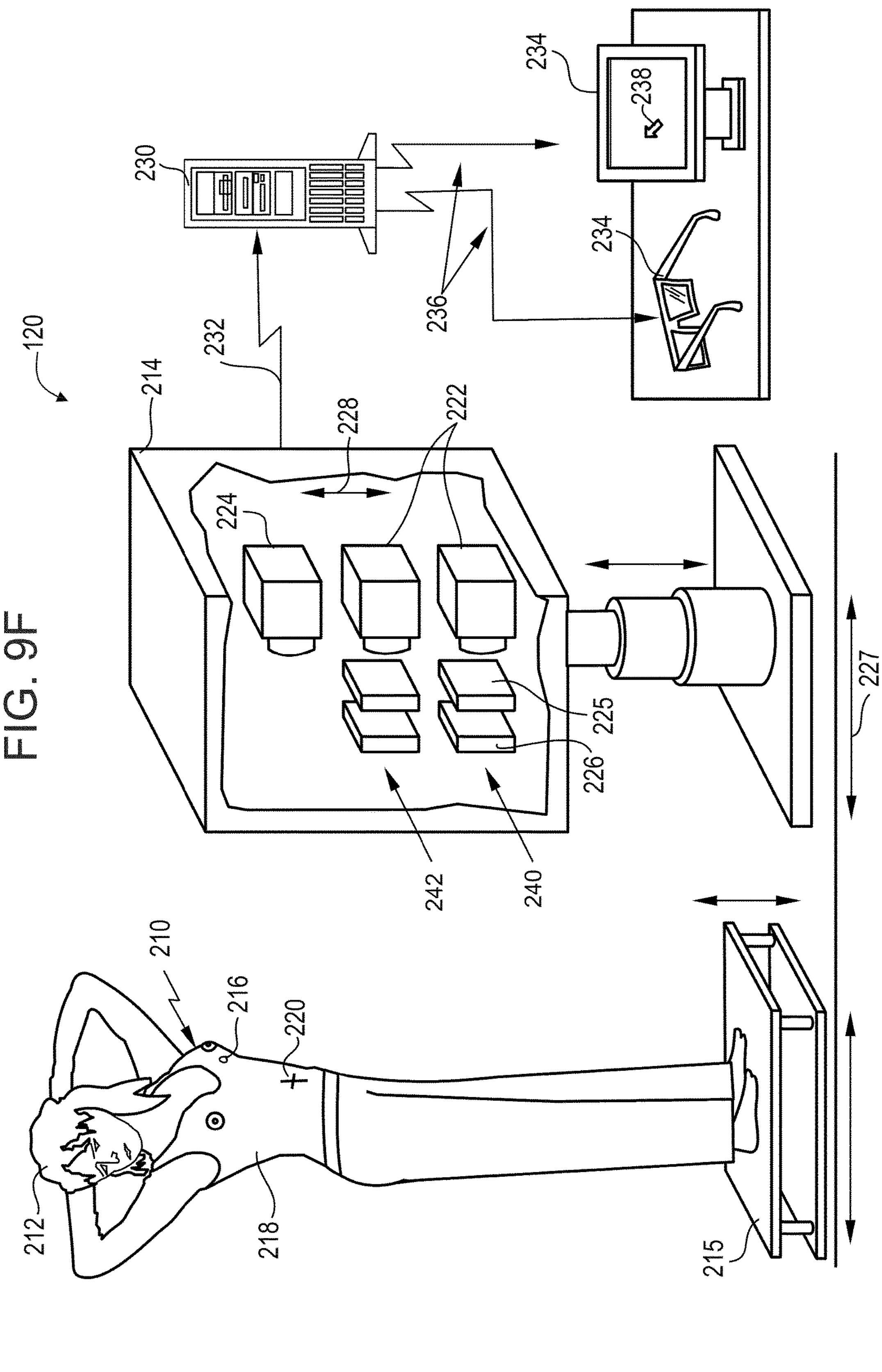

The second relative position 242 may be configured by repositioning person 212 using positioning device 215 as seen in FIG. 9*b*, by repositioning imaging device 214 using positioning device 227 as seen in FIG. 9*c* or by repositioning imaging device 222 using positioning device 228 as seen in FIG. 9*d*. As a further alternative, second relative position 242 may be configured by using two separate imaging devices 214 as seen in FIG. 9*e* or two separate visible light imaging device 222 as seen in FIG. 9*f*.

Referring to FIGS. 10*a-e*, person 212 comprising body 210 is located on positioning device 215 in front of imaging device 214, in a first position 244 relative to the imaging device. First thermographic image data of body 210 is acquired by thermographic imaging device 224. Optionally and preferably at least second thermographic image data of body 210 is acquired by thermographic imaging device 224, such that body 210 is positioned in at least a second position 242 relative to imaging device 214. Thus, the first, second and optionally more thermographic image data are acquired from at least two different viewpoints of the thermographic imaging device relative to body 210.

Figure 10A:
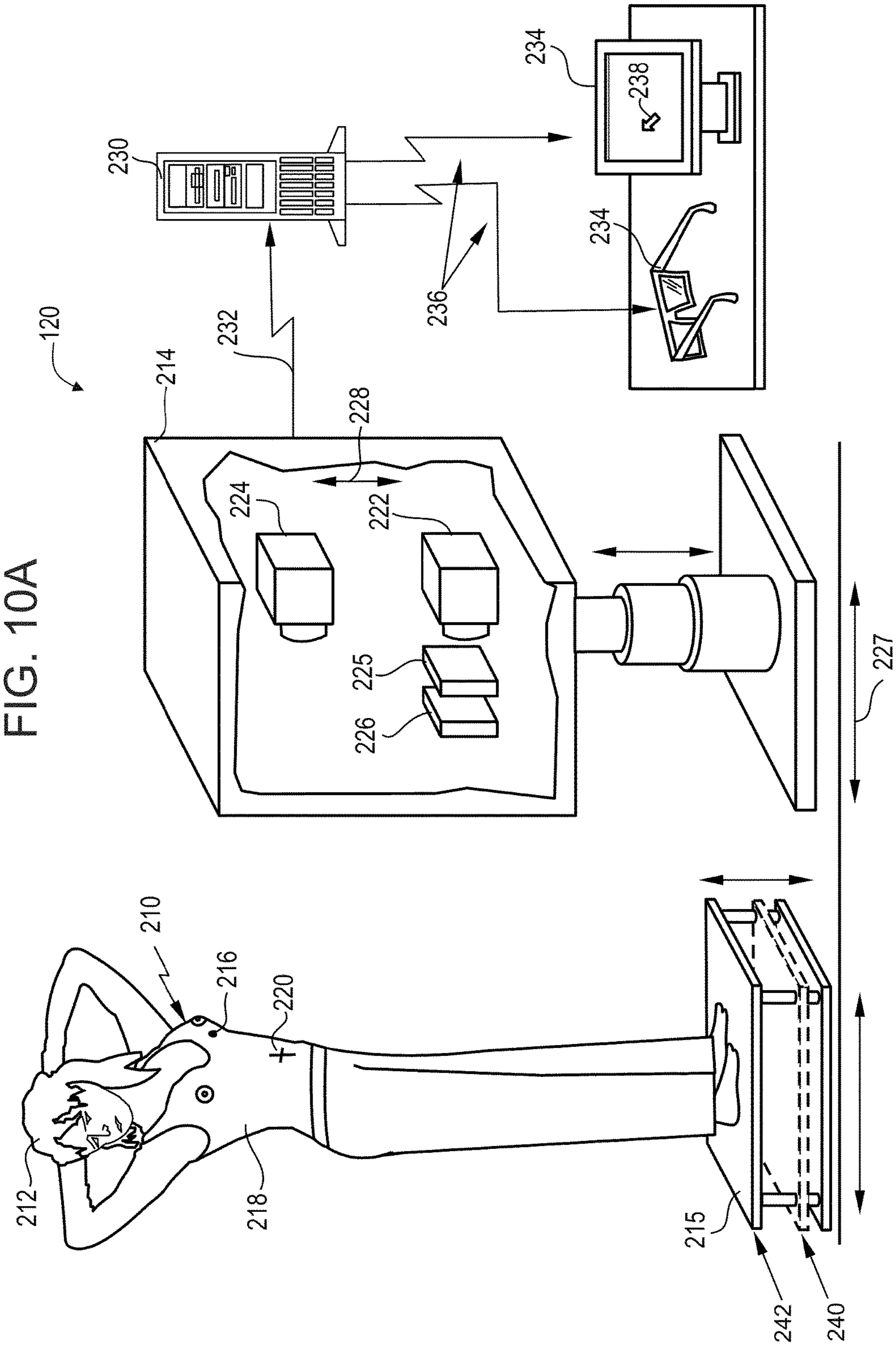
Figure 10B:
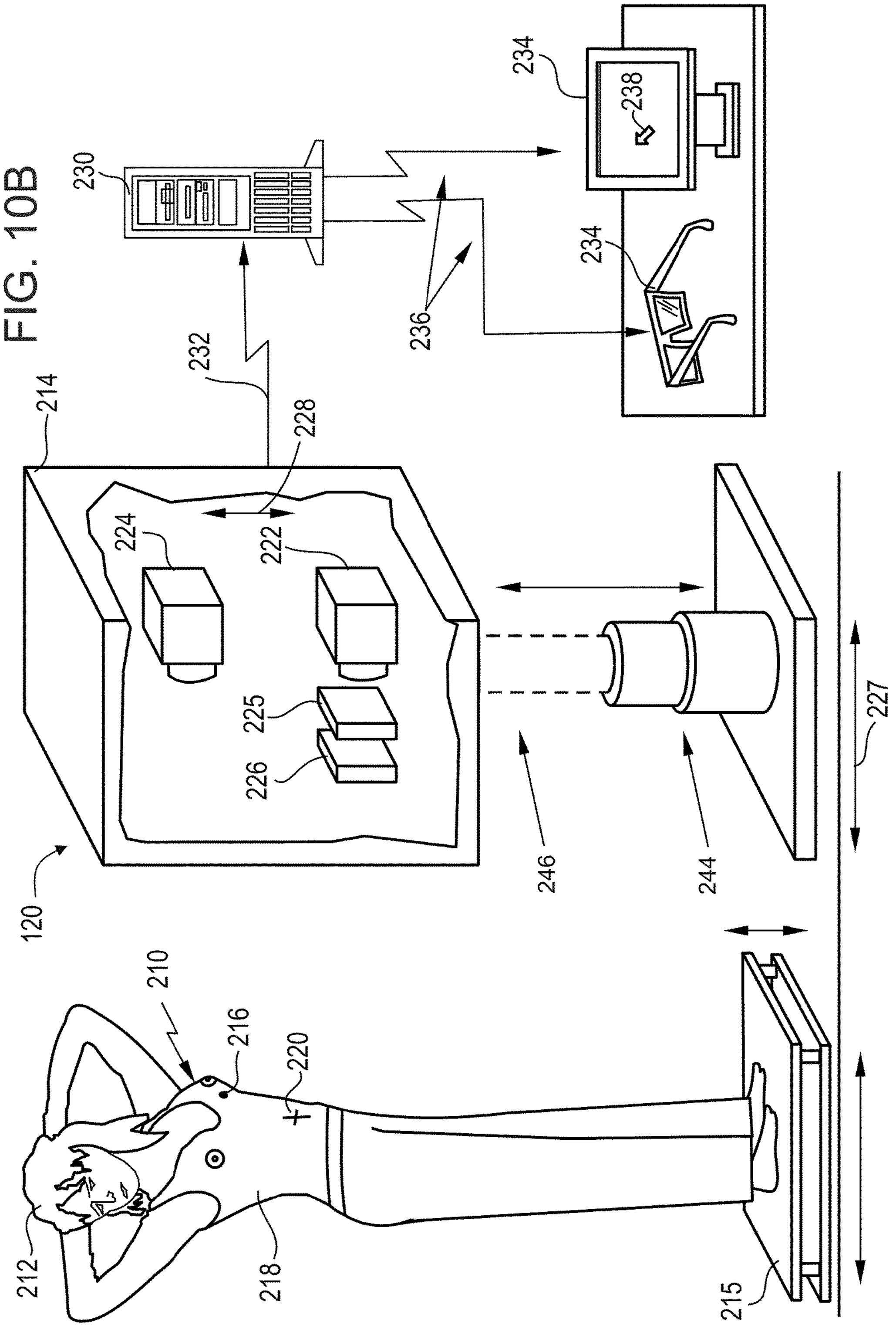
Figure 10C:
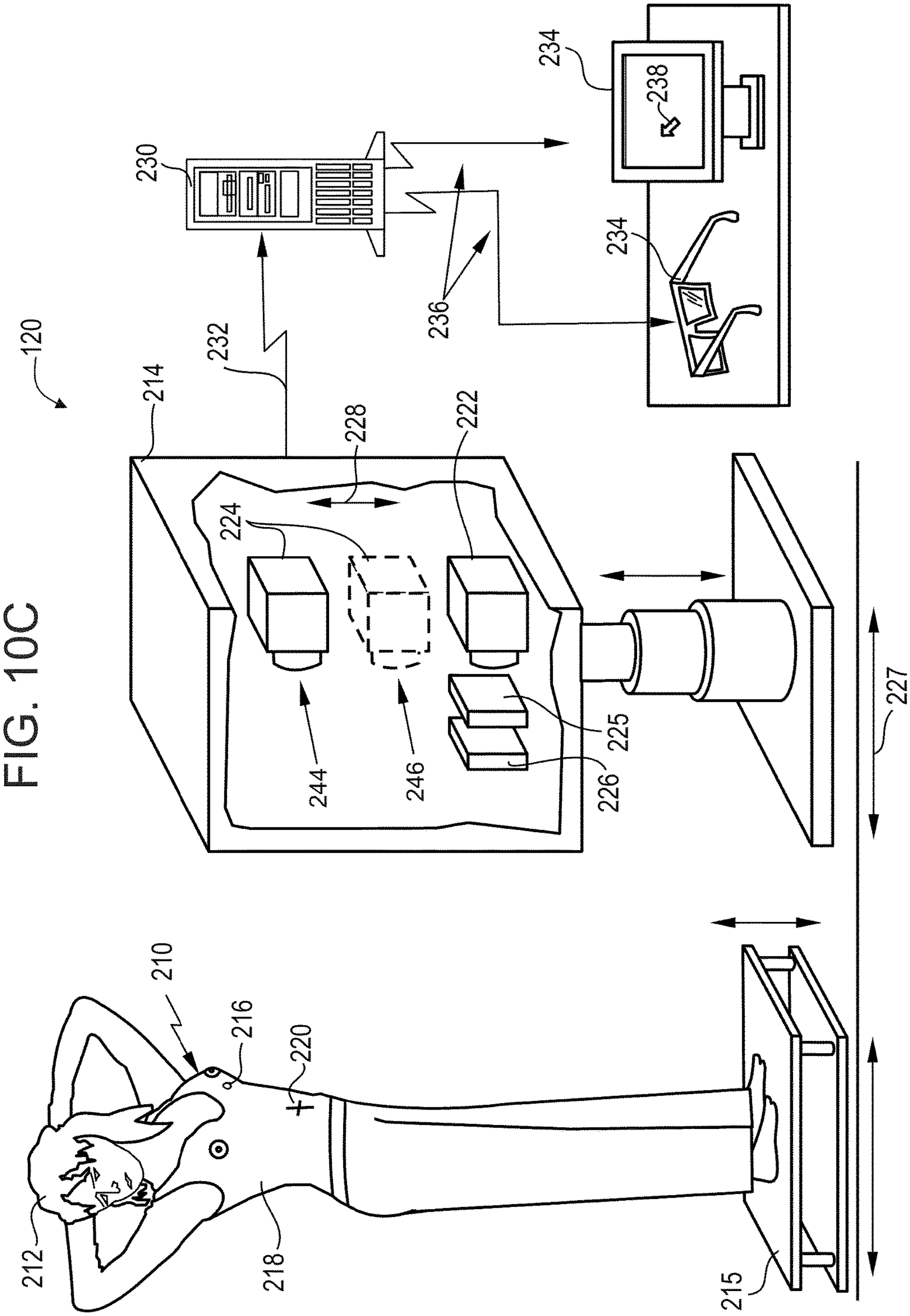
Figure 10D:
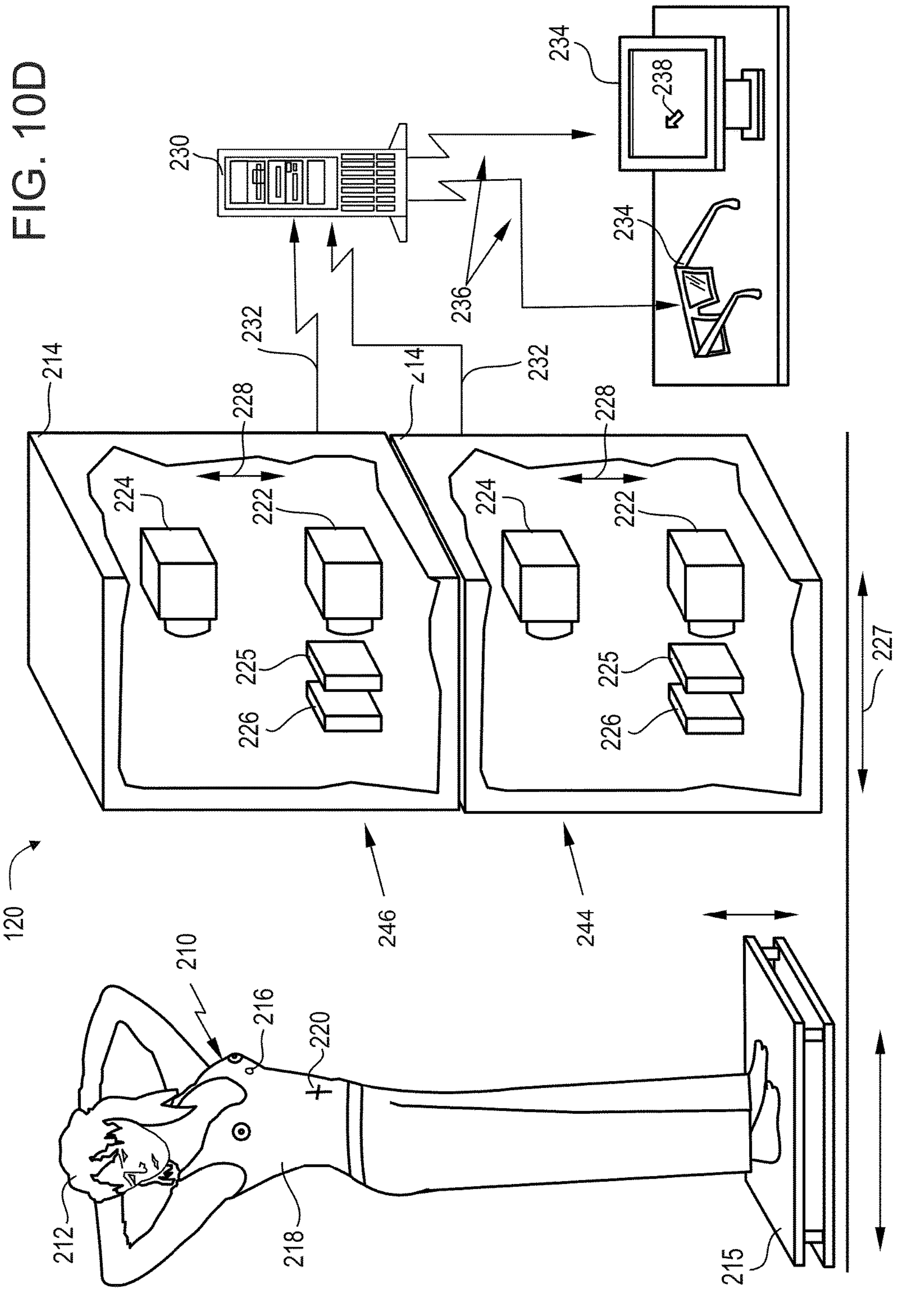
Figure 10E:
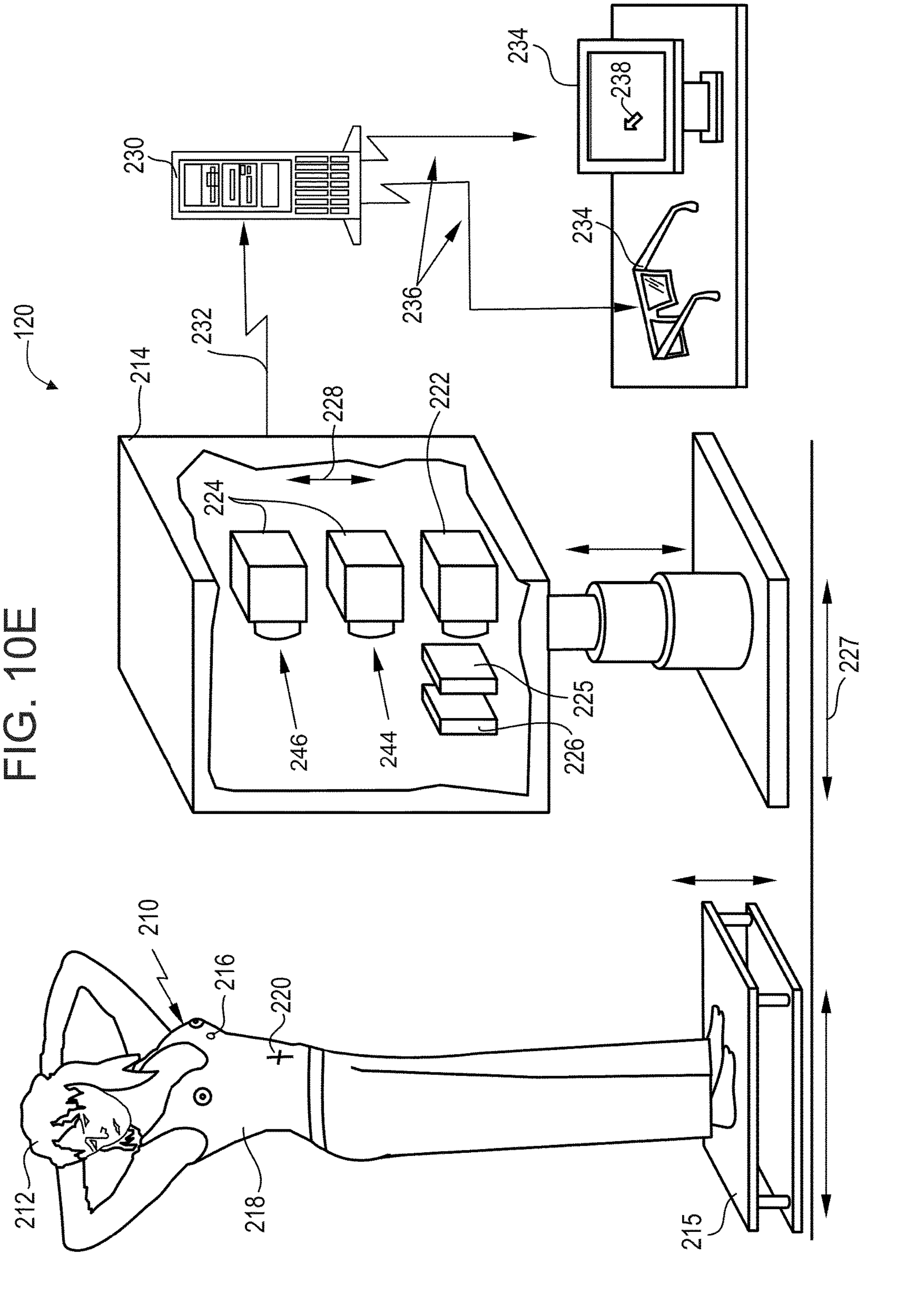

The second relative position 246 may be configured by repositioning person 212 using positioning device 215 as seen in FIG. 10*a*, by repositioning imaging device 214 using positioning device 227 as seen in FIG. 10*b*, or by repositioning thermographic imaging device 224 using positioning device 228 as seen in FIG. 10*c*. As a further alternative, the second relative position 246 may be configured by using two separate imaging devices 214 as seen in FIG. 10*d* or two separate thermographic imaging devices 224 as seen in FIG. 10*e*.

Image data of body 210 may be acquired by thermographic imaging device 224, by separately imaging a plurality of narrow strips of the complete image of body 210. Alternatively, the complete image of body 210 is acquired by the thermographic imaging device, and the image is sampled in a plurality of narrow strips or otherwise shaped portions for processing. As a further alternative, the imaging of body 210 may be performed using different exposure times.

The thermographic and visible light image data obtained from imaging device 214 is preferably analyzed and processed by data processor 230 as follows. Image data acquired from imaging device 222 is processed by data processor 230 to build a three-dimensional spatial representation of body 210, using algorithms and methods that are well known in the art, such as the method described in U.S.

Pat. No. 6,442,419 which is hereby incorporated by reference as if fully set forth herein. The 3D spatial representation preferably comprises the location of reference marker 220 (cf. FIG. 1*a*). Optionally and preferably, the 3D spatial representation comprises information relating to the color, hue and tissue texture of body 210. Thermographic image data acquired from imaging device 224 is processed by data processor 230 to build a thermographic three-dimensional model of body 210, using algorithms and methods that are well known in the art, such as the method described in U.S. Pat. No. 6,442,419. The thermographic 3D model preferably comprises reference marker 220 (cf. FIG. 1*b*). The thermographic 3D model is then mapped by processor 230 onto the 3D spatial representation, e.g., by aligning reference marker 220, to form the thermospatial image.

As used herein the term "about" refers to ±10%.

The terms "comprises", "comprising", "includes", "including", "having" and their conjugates mean "including but not limited to".

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of identifying an internal thermally distinguishable region in a living body comprising:

operating a thermospatial imaging system for imaging the living body and generating and storing in a memory a first thermospatial image describing a section of the living body when the living body is at a first posture, and a second thermospatial image describing said section of the living body when the living body is at a second posture, wherein each thermospatial image is defined over a three-dimensional (3D) spatial image of said body and has thermal data associated with a surface of the 3D spatial image;

retrieving said thermospatial images from said memory;

using a data processor of a computing platform for calculating a deformation function which maps a first 3D shape of said section of the living body, corresponding to said first posture, to a second 3D shape of said section of the living body, corresponding to said second posture, to determine correspondence between sets of picture-elements belonging to said first and said second thermospatial images;

determining, by said computing platform, transient thermal variation for each picture-element in at least one set and storing said transient thermal variation in the memory; and estimating, by said computing platform, a location or presence of the internal thermally distinguishable region in the living body based on said transient thermal variations and generating, by said computing platform, an output indicative of the internal thermally distinguishable region.

2. The method of claim 1, further comprising estimating, by said computing platform, a size of said internal thermally distinguishable region, based on said transient thermal variation.

3. The method of claim 1, further comprising comparing, by said computing platform, said transient thermal variation to a reference transient thermal history, so as to determine said presence of said internal thermally distinguishable region.

4. The method of claim 1, further comprising heating or cooling a surface of said section of the living body between said first and said second thermospatial images.

5. The method of claim 1, wherein said estimating said location of said internal thermally distinguishable region comprises determining, by said computing platform, amount of temperature change for each point of a plurality of points over a surface of said section of the living body.

6. The method of claim 5, wherein said estimating said location of said internal thermally distinguishable region comprises determining, by said computing platform, a temperature change rate for at least one point of said plurality of points.

7. The method of claim 6, wherein said estimating said location of said internal thermally distinguishable region comprises comparing, by said computing platform, a temperature change rate of one point of said plurality of points to a temperature change rate of another point of said plurality of points.

8. The method of claim 5, wherein said estimating said location of said internal thermally distinguishable region comprises determining, by said computing platform, onset of a steady thermal state for at least one point of said plurality of points.

9. The method of claim 5, wherein said estimating said location of said internal thermally distinguishable region comprises determining, by said computing platform, onset of temperature change for at least one point of said plurality of points.

10. The method of claim 1, further comprising estimating, by said computing platform, characteristic heat conduction of said section of the living body based on said first thermospatial image and said second thermospatial image.

11. The method of claim 1, wherein said section of the living body is a breast of a woman.

12. The method of claim 1, further comprising determining, by said computing platform and based on said transient thermal variation, whether a point on said section of the living body corresponding to said picture-element has moved closer to or farther from the internal thermally distinguishable region between said first posture and said second posture, wherein said estimating said location or presence of the internal thermally distinguishable region is based on whether said point is closer to or farther from the internal thermally distinguishable region.

13. A method of treating a tumor in a body section, the tumor being the internal thermally distinguishable region of claim 2, the method comprising:

(a) executing the method of claim 2 to estimate a size of the tumor;

(b) applying a destructive treatment to the tumor; and (c) executing the method of claim 2 to re-estimate said size.

14. The method of claim 13, further comprising repeating said (b) and said (c) until said size satisfies a predetermined criterion.

15. A method of monitoring evolution of a tumor in a body section, the tumor being the internal thermally distinguishable region of claim 2, the method comprising executing the method of claim 2 a plurality of times to estimate a size of the tumor at each execution, thereby monitoring the evolution of the tumor.

16. Apparatus for locating an internal thermally distinguishable region within a living body, comprising:

an input for receiving a first thermospatial image describing a section of the living body when the living body is at a first posture, and a second thermospatial image describing said section of a living body, wherein each thermospatial image is defined over a three-dimensional (3D) spatial image of said body and has thermal data associated with a surface of the 3D spatial image; and a computing platform configured for calculating a deformation function which maps a first 3D shape of said section of the living body, corresponding to said first posture, to a second 3D shape of said section of the living body, corresponding to said second posture, to determine correspondence between sets of picture-elements belonging to said first and said second thermospatial images, determining by the computing platform, transient thermal variation for each picture-element in at least set, and estimating, by the computing platform, a location or presence of the internal thermally distinguishable region in said section of the living body based on said transient thermal variations.

17. The apparatus or system of claim 16, wherein said computing platform is configured for estimating a size of said internal thermally distinguishable region, based on said transient thermal variation.

18. The apparatus or system of claim 16, wherein said computing platform is configured for comparing said transient thermal variation to a reference transient thermal history, so as to determine said presence of said internal thermally distinguishable region.

19. The apparatus of claim 16, wherein said computing platform is configured for estimating characteristic heat conduction of said section of the living body based on said first thermospatial image and said second thermospatial image.

20. The apparatus of claim 16, wherein said computing platform configured for determining, based on said transient thermal variation, whether a point on said section of the living body corresponding to said picture-element has moved closer to or farther from the internal thermally distinguishable region between said first posture and said second posture, wherein said estimating said location or presence of the internal thermally distinguishable region is based on whether said point is closer to or farther from the internal thermally distinguishable region.

21. An imaging and processing system, comprising the apparatus of claim 16 and a thermospatial imaging system operable to provide said input unit with said thermospatial images.

* * * * *